(12) United States Patent
Mullen et al.

(10) Patent No.: US 10,214,505 B2
(45) Date of Patent: Feb. 26, 2019

(54) KETAL ESTER COMPOUNDS AND USES THEREOF

(71) Applicant: GFBiochemicals Limited, Valletta (MT)

(72) Inventors: Brian D. Mullen, Delano, MN (US); Dorie J. Yontz, Bloomington, MN (US); Erich J. Molitor, Midland, MI (US)

(73) Assignee: GFBIOCHEMICALS LIMITED, Valletta (MT)

( * ) Notice: Subject to any disclaimer, the term of this patent is extended or adjusted under 35 U.S.C. 154(b) by 0 days.

(21) Appl. No.: 15/528,235

(22) PCT Filed: Nov. 19, 2015

(86) PCT No.: PCT/US2015/061470
§ 371 (c)(1),
(2) Date: May 19, 2017

(87) PCT Pub. No.: WO2016/081683
PCT Pub. Date: May 26, 2016

(65) Prior Publication Data
US 2017/0342045 A1 Nov. 30, 2017

Related U.S. Application Data

(60) Provisional application No. 62/082,250, filed on Nov. 20, 2014.

(51) Int. Cl.
C07D 317/30 (2006.01)
C08K 5/10 (2006.01)
(52) U.S. Cl.
CPC .............. *C07D 317/30* (2013.01); *C08K 5/10* (2013.01)

(58) Field of Classification Search
CPC ................................ C07D 317/30; C08K 5/10
See application file for complete search history.

(56) References Cited

U.S. PATENT DOCUMENTS

2008/0242721 A1* 10/2008 Selifonov ............ C07D 317/30
514/467

FOREIGN PATENT DOCUMENTS

| WO | 2007062118 A2 | 5/2007 |
| WO | 2009032905 A1 | 3/2009 |
| WO | 2010036884 A1 | 4/2010 |
| WO | 2013055781 A1 | 4/2013 |
| WO | 2014085609 A1 | 6/2014 |

OTHER PUBLICATIONS

International Search Report for International Application No. PCT/US2015/061470, International Filing Date Nov. 19, 2015, dated Jun. 22, 2016, 5 pages.
Mullen, Brian D., et al., "Catalytic Seiectiivity of Ketalization Versus Transesterification", Topics in Catalysis, vol. 53, No. 15-18, May 28, 2010, pp. 1235-1240.
Written Opinion for International Application No. PCT/US2015/061470, International Filing Date Nov. 19, 2015, dated Jun. 22, 2016, 7 pages.
Supplementary European Search Report for European Application No. 15861180.6 dated Jun. 18, 2018, 6 pages.

* cited by examiner

*Primary Examiner* — Timothy R Rozof
(74) *Attorney, Agent, or Firm* — Cantor Colburn LLP

(57) ABSTRACT

The invention describes methods of preparation and compositions of plasticizers. The ketal diester products described are useful as components of polymer compositions. The products are excellent plasticizers for a variety of polymers, such as poly(vinylchloride) plastisols.

19 Claims, No Drawings

KETAL ESTER COMPOUNDS AND USES THEREOF

CROSS REFERENCE TO RELATED APPLICATIONS

This application is a National Stage application of PCT/US15/61470, filed Nov. 19, 2015, which claims the benefit of U.S. Provisional Application No. 62/082,250, filed Nov. 20, 2014, both of which are incorporated by reference in their entirety herein.

FIELD OF THE INVENTION

The invention relates generally to alkyl ketal esters as well as their method of making and using. The alkyl ketal esters have use as plasticizers in polymeric formulations.

BACKGROUND OF THE INVENTION

Many known chemical products such as surfactants, plasticizers, solvents, and polymers are currently manufactured from non-renewable, expensive, petroleum-derived or natural gas-derived feedstock compounds. Phthalate esters, particularly, dioctyl phthalate ester, di(2-ethylhexyl) phthalate ester, and diisononyl phthalate ester are industrially significant plasticizers useful for plasticizing many formulations; more common formulations include those containing poly (vinyl chloride) (PVC). Recent regulatory pressure has targeted phthalates (United States Environmental Protection Agency Report: Phthalates Action Plan—Dec. 30, 2009) for replacement due to the risks associated with their use. Plasticizer replacements are needed to plasticize formulations without the risk to humans, animals and the environment.

High raw material costs and uncertainty of future supplies requires the discovery and development of surfactants, plasticizers, solvents, and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

The use of levulinate compounds and glycerol based compounds is particularly useful as both of these starting materials arise from renewable feedstocks. Further, the ketal reaction products are useful for synthesis of a wide variety of surfactants, plasticizers, polymers, and the like. Other reaction products of oxocarboxylates (such as pyruvic acid, acetoacetic acid, or esters thereof, and the like) with triols (such as trimethylolpropane, trimethylolethane, and the like) are disclosed in International Patent Application No. PCT/US08/75225.

BRIEF SUMMARY OF THE INVENTION

It is desirable to provide commonly used materials, such as surfactants, plasticizers, solvents, and polymers, from renewable feedstocks as a source of chemical building blocks. It is also desirable to provide chemical building blocks that are chemically and thermally stable. Furthermore, chemical building blocks having multiple functionalities for subsequent reactions are often desirable. The ability to provide such materials by simple and reproducible methods that can be carried out with ease is advantageous.

The present invention provides compositions of alkyl ketal ester compounds.

In one aspect, the invention is a compound having a structure corresponding to Structure I:

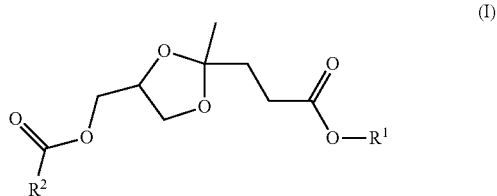

(I)

wherein R1 is a linear, branched, or cyclic alkyl or aryl group comprising 2 to 18 carbon atoms and no oxygen atoms, and R2 is a linear, branched, or cyclic alkyl or aryl group comprising 1 to 17 carbon atoms and no oxygen atoms. In one embodiment, the invention is a mixture comprising two or more compounds having Structure I.

In another aspect, the invention is a plasticizer composition comprising a compound having Structure I.

In another aspect, the invention is a composition comprising a polymer and a compound or mixture of compounds of Structure I.

In another aspect, the invention is an article comprising the compositions described above.

In another aspect, the invention is a composition comprising the product of a polyvinyl chloride material and a blend comprising a compound or mixture of compounds of Structure I and at least one other plasticizer, wherein the composition comprises from 20 to 200 parts of the compound of Structure I and the at least one other plasticizer, per 100 parts of the polyvinyl chloride material (parts being by weight).

In another aspect, the invention is an article comprising the compositions described above.

In another aspect, the invention is a plastisol including a compound of Structure I.

In another aspect, the invention is an article produced from a plastisol including a compound of Structure I, wherein the plastisol is processed through plastisol coating of substrates, dipping, spraying, spreading, rotational molded, casting, or pouring to form the article.

In another aspect, the invention is an article comprising wire or cable and a coating, the coating comprising PVC and a plasticizer comprising from 30 to 60 wt % based upon the total weight of the plasticizer of a compound of Structure I.

In another aspect, the invention is a car having an interior part comprising PVC and a plasticizer comprising from 30 to 60 wt % based upon the total weight of the plasticizer of a compound of Structure I.

In another aspect, the invention is a film produced from a plastisol comprising PVC and a plasticizer comprising from 30 to 60 wt % based upon the total weight of the plasticizer of a compound of Structure I.

In another aspect, the invention is a multilayer article in which at least two adjacent layers comprise plasticized polyvinyl chloride wherein the plasticizer in one of the two adjacent layers contains a compound of Structure I.

In another aspect, the invention is an article selected from a medical tubing, a blood bag, a toy and a material used for food contact, the article comprising PVC plasticized with a compound of Structure I, wherein the article comprises a plurality of layers and wherein at least two adjacent layers comprise plasticized polyvinyl chloride wherein the plasticizer in one of the two adjacent layers contains the compound of Structure I, and wherein the other of the two adjacent layers contains a compound selected from phthalate esters, dialkyl phthalates, trimethyl pentanyl diisobutyrate, dialkyl isophthalates, dialkyl terephthalates, alkyl benzyl phthalates, alkyl benzyl terephthalates, dibenzyl phthalates, dibenzyl terephthalates, dialkyl adipates, dialkyl succinates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, monobenzoates, dibenzoates, epoxidized seed oils (such as epoxidized soybean oil or epoxidized linseed oil), chlorinated paraffins, diglycerides, triglycerides, polyketals, and mixtures thereof.

In another aspect, the invention is a polyvinyl chloride composition comprising 100 parts of polyvinyl chloride and from 20 to 200 parts of total plasticizer comprising a plasticizer comprising a first compound of Structure I and 7 to 30 wt %, based on the weight of the total plasticizer, of a second compound selected from phthalate esters, dialkyl phthalates, trimethyl pentanyl diisobutyrate, dialkyl isophthalates, dialkyl terephthalates, alkyl benzyl phthalates, alkyl benzyl terephthalates, dibenzyl phthalates, dibenzyl terephthalates, dialkyl adipates, dialkyl succinates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, monobenzoates, dibenzoates, epoxidized seed oils (such as epoxidized soybean oil or epoxidized linseed oil), chlorinated paraffins, diglycerides, triglycerides, polyketals, and mixtures thereof.

In another aspect, the invention is a polyvinyl chloride composition comprising 100 parts of polyvinyl chloride and from 20 to 200 parts of total plasticizer comprising a plasticizer other than an ester of a cyclohexane carboxylic acid and 7 to 30 wt %, based on the weight of the total plasticizer, of a compound of Structure I.

In another aspect, the invention is a mixture of esters of Structure I,

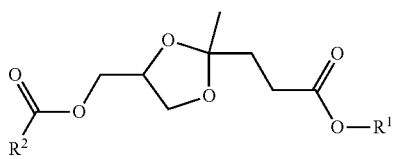

(I)

in which each of $R^1$ and $R^2$ is an aliphatic C5 or C9 moiety, wherein the average chain length of the aliphatic moieties in the mixture is in the range of 5 to 7, and the average degree of branching of the aliphatic C9 moieties is in the range of from 0.9 to 2.2. In one embodiment, the mixture is a plasticizer composition.

In another aspect, the invention is a mixture, comprising: at least two different diesters of Structure I:

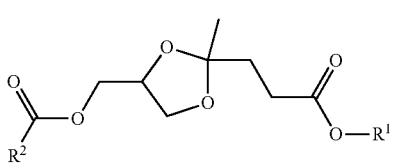

(I)

wherein each of $R^1$ and $R^2$ is independently an alkyl group having from 6 to 10 carbon atoms, and $R^1$ and $R^2$ groups of at least two of the diesters of Structure I are nonidentical isomers.

In another aspect, the invention is a paint, an ink, a coating, a plastisol, an adhesive, a component of an adhesive, a sealing composition, a plasticizer in a plastic, a plasticizer in a component of a plastic, a solvent, a component of a lubricating oil, or an auxiliary during metalworking, comprising the mixture above.

In another aspect, the invention is a PVC plastic or component thereof, comprising the mixture above.

In another aspect, the invention is a PVC plastisol, comprising the mixture above.

In another aspect, the invention is a PVC composition, comprising PVC and the mixture above, wherein the composition has a content of from 5 to 250 parts by weight of the mixture above per 100 parts by weight of PVC.

In another aspect, the invention is a plastisol, comprising: PVC and the mixture above, wherein the composition has a content of from 5 to 250 parts by weight of the mixture above per 100 parts by weight of PVC.

In another aspect, the invention is a method for making an ester compound having Structure I

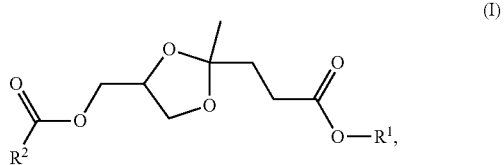

(I)

comprising the steps of contacting reagents comprising one or more alkyl ketal esters having Structure II

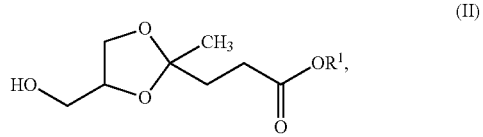

(II)

a catalyst and an alkyl halide under reaction conditions to form the compound of Structure I, wherein $R^1$ is a linear, branched, or cyclic alkyl or aryl group comprising 2 to 18 carbon atoms and no oxygen atoms, and $R^2$ is a linear, branched, or cyclic alkyl or aryl group comprising 1 to 17 carbon atoms and no oxygen atoms.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present disclosure provides a series of alkyl ketal esters derived from glycerol-levulinate ketal compounds.

In one aspect, the invention is a compound having a structure corresponding to Structure I:

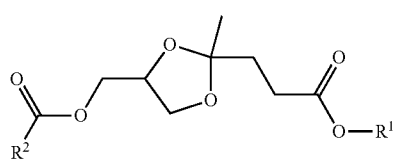

(I)

wherein $R^1$ is a linear, branched, or cyclic alkyl or aryl group comprising 2 to 18 carbon atoms and no oxygen atoms, and $R^2$ is a linear, branched, or cyclic alkyl or aryl group comprising 1 to 17 carbon atoms and no oxygen atoms.

In specific embodiments, $R^1$ comprises 2 to 4 carbon atoms, 8 to 12 carbon atoms, or 14 to 18 carbon atoms. In more specific embodiments $R^1$ comprises 8 carbon atoms, 9 carbon atoms, 10 carbon atoms, or 12 carbon atoms.

In other specific embodiments, $R^2$ comprises 1 carbon atom, 5 carbon atoms, 7 carbon atoms, 9 carbon atoms, 11 carbon atoms, 13-17 carbon atoms, benzyl or an aryl group.

In other specific embodiments, the compound of Structure I includes any combination of $R^1$ and $R^2$ described above, such as where $R^1$ comprises 12 carbon atoms and $R^2$ is a benzyl group.

In a specific embodiment, the compound of Structure I is a structure corresponding to Structure (Ia):

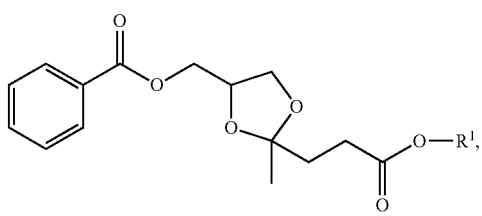

(Ia)

wherein $R^1$ is as defined above.

Some specific embodiments of Structure (Ia) include:

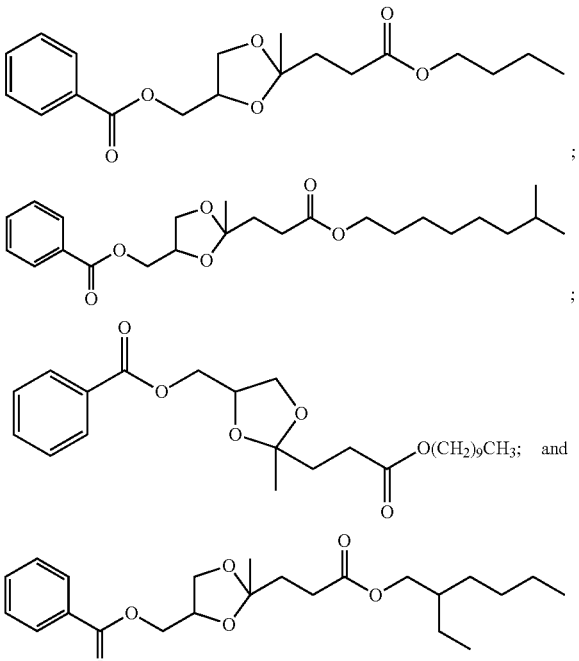

In another specific embodiment, the compound of Structure I is a structure corresponding to structure (Ib), (Ic), or (Id):

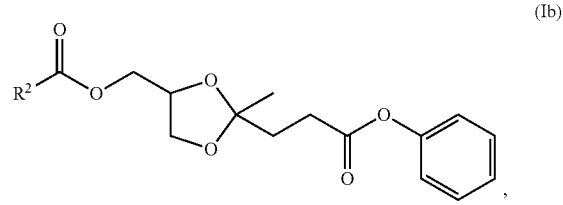

(Ib)

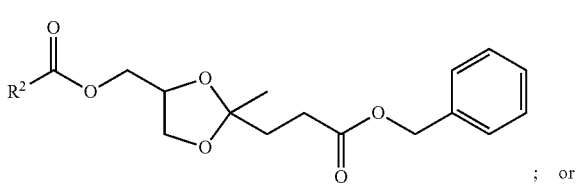

(Ic)

; or

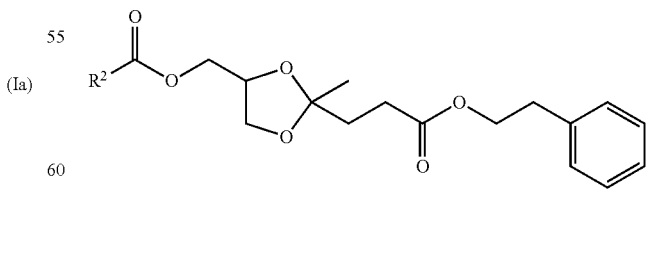

(Id)

wherein $R^2$ is as defined above.

Other specific embodiments of Structure (I) include the following:

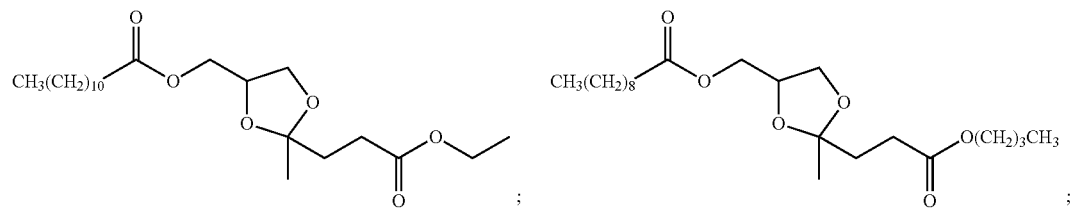
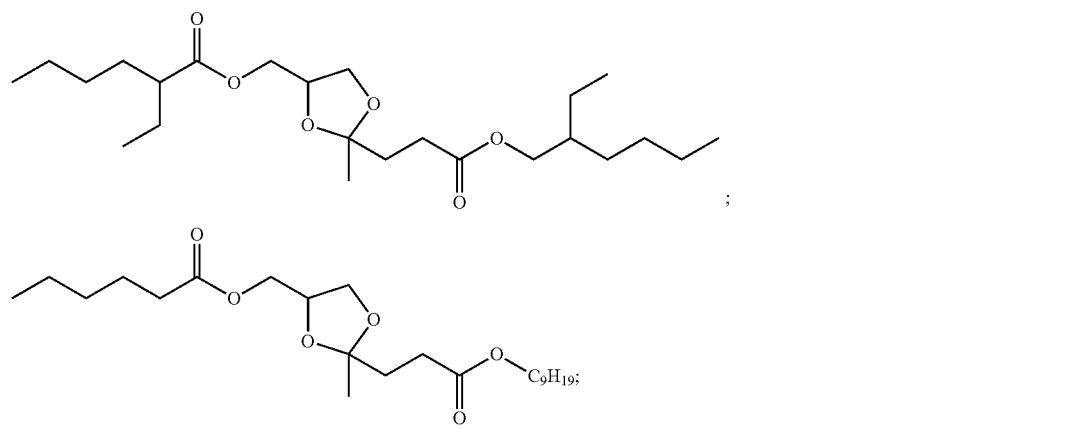
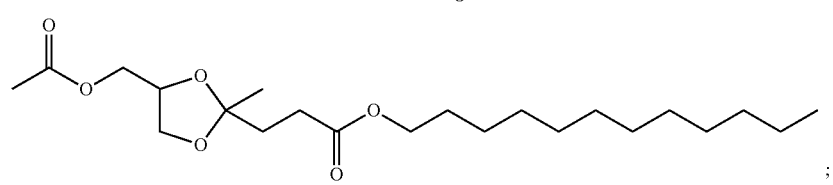
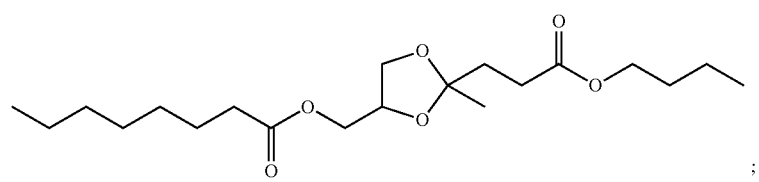
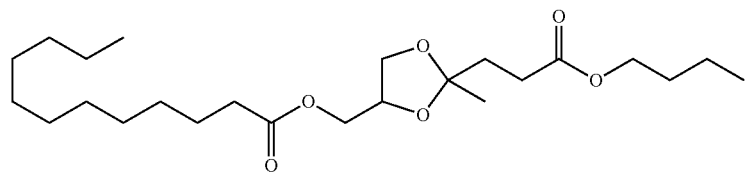
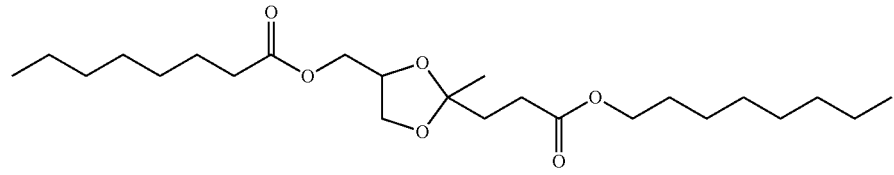
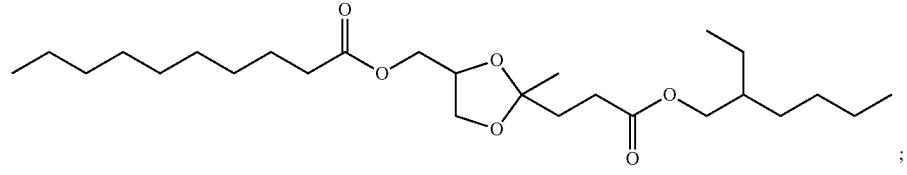
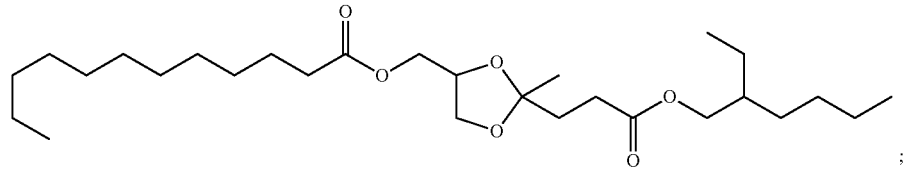

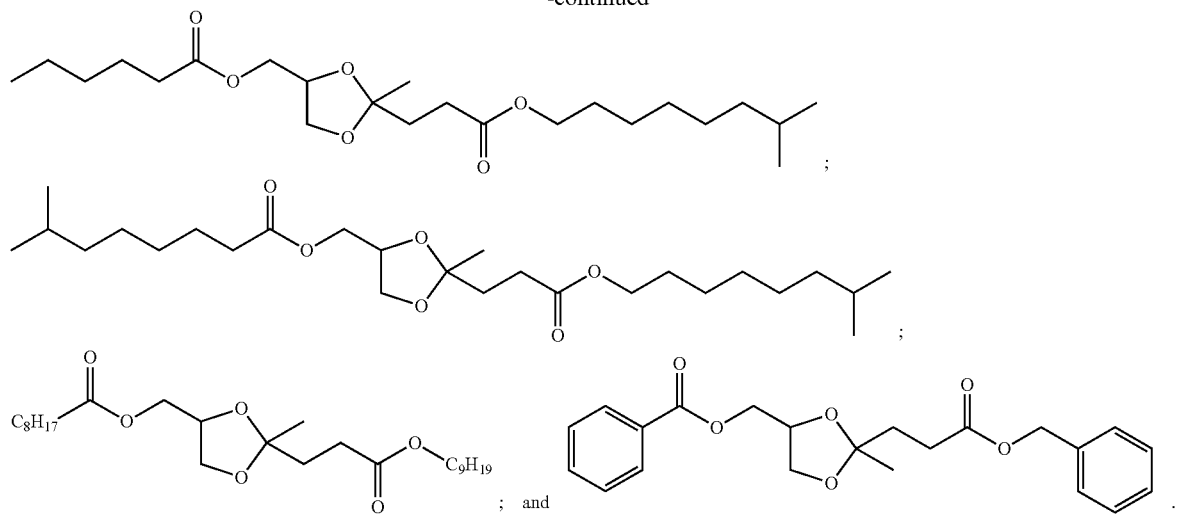
; and

In another aspect, the invention is a mixture comprising at least two different compounds according to Structure I.

In one embodiment, the mixture is such that each of $R^1$ and $R^2$ is an aliphatic C5 or C9 moiety, wherein the average chain length of the aliphatic moieties in the mixture is in the range of 5 to 7, more specifically, 5.5 to 6.8, and the average degree of branching of the aliphatic C9 moieties is in the range of from 0.9 to 2.2, more specifically, 1.0 to 2.0. In one embodiment, the C5 moieties comprise at least 50%, more specifically, at least 60%, more specifically, at least 70%, more specifically, at least 80%, and more specifically, at least 90% of n-pentyl and 3-methylbutyl moieties, based on the entirety of the C5 moieties. In another embodiment, the C5 moieties comprise at least 50%, more specifically, at least 60%, and more specifically, at least 70% of 3-methylbutyl moieties, based on the entirety of the C5 moieties.

In one embodiment, the mixture is such that each of $R^1$ and $R^2$ is independently an alkyl group having from 6 to 10 carbon atoms, and the $R^1$ and $R^2$ groups of at least two of the diesters of Structure I are non-identical isomers. In one embodiment, a proportion of the $R^1$ and $R^2$ groups of any one structure is not more than 95 mol % of all of the $R^1$ and $R^2$ groups in the mixture. In one embodiment, less than 10 mol % of the $R^1$ and $R^2$ groups in the mixture are 3,5,5-trimethylpentyl groups. In another embodiment, the $R^1$ and $R^2$ groups of the mixture have an average degree of branching of from 0.7 to 2.0, more specifically, 1.2 to 1.9. In another embodiment, the diesters comprise at least two different bicyclic substructures of Structure I, which differ in configuration. In another embodiment, the mixture includes at least two diesters with different molar masses. In another embodiment, the diesters in the mixture all comprise identical bicyclic substructures of Structure I, and individual diester isomers differ only via differently structured $R^1$ and $R^2$ groups. In another embodiment, the two different diesters are diesters of isosorbide.

In another aspect, the invention is a method for making an ester compound according to Structure I comprising the steps of contacting reagents comprising:

(A) one or more alkyl ketal esters having the structure (II)

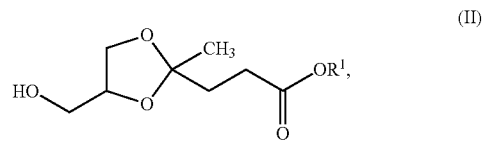

(B) a catalyst; and
(C) an alkyl halide under reaction conditions to form the compound of Structure I, wherein $R^1$ is as defined above, specifically, methyl, ethyl, n-propyl, n-butyl, 2-ethyl-1-hexyl, octyl, and dodecyl.

In one embodiment, the catalyst is a stoichiometric excess of a catalytic amine or tertiary amine.

When $R^1$ is methyl, this structure is referred to herein as "methyl-LGK," and corresponds to the reaction formulation of methyl levulinate with glycerine. Methyl-LGK is miscible with water in all proportions.

When $R^1$ in Structure II is ethyl, this structure is referred to herein as "ethyl-LGK," or "Et-LGK" and corresponds to the reaction formulation of ethyl levulinate with glycerine. Ethyl-LGK is miscible in water in all proportions. Ethyl-LGK also dissolves or is miscible with a large number of hydrophobic and hydrophilic organic compounds to the extent of at least 20 parts of the organic compound in 80 parts of ethyl-LGK. Examples of such organic compounds include methanol, ethanol, tetrahydrofuran, acetone, ethyl acetate, ethyl laurate, lauric acid, methylene chloride, toluene, acetic acid, low molecular weight poly(propylene glycol), and castor oil.

When $R^1$ in Structure II is n-propyl, this structure is referred to herein as "n-propyl-LGK," and corresponds to the reaction formulation of n-propyl levulinate with glycerine. n-Propyl-LGK is miscible with water to the extent of 1 part per 99 parts water.

When $R^1$ in Structure II is n-butyl, this structure is referred to herein as "n-butyl-LGK" or "Bu-LGK," and represents the reaction formulation of n-butyl levulinate with glycerine. n-Butyl-LGK is miscible in water to the extent of 1 part per 99 parts of water. It dissolves or is miscible with various organic compounds to the extent of at least 20 parts of the organic compound in 80 parts of N-butyl-LGK. Examples of such organic compounds include alcohols (including ethanol and 1,2-butylene glycol), organic esters (such as C12-14 alkyl benzoates, isopropyl myristate and octyl palmitate), and many vegetable oils (including castor, corn, soy and safflower oils).

When $R^1$ in Structure II is octyl, this structure is referred to herein as "octyl-LGK" or and represents the reaction formulation of octyl levulinate with glycerine.

When $R^1$ in Structure II is dodecyl, this structure is referred to herein as "dodecyl-LGK" and represents the reaction formulation of dodecyl levulinate with glycerine.

In an embodiment, the trans-esterification in the presence of base is carried out under conditions similar to that for an alcoholic trans-esterification, except that instead of an alcohol, an ester of a carboxylic acid and an alkanol is used. In this case, stereoisomers of carboxylic esters of glycerol levulinate ketal of Structure I are formed.

The synthesis of compounds of Structure I using trans-esterification with the carboxylic ester is also typically accompanied by the formation of minor quantities of levulinate ester, glycerol, glycerol mono, di and tri esters of the carboxylic acid $R^2COOH$, and varying quantities of other compounds. The reaction products from base-catalyzed trans-esterification with carboxylic esters are typically separated and purified by distillation.

In one aspect, the invention is a plasticizer composition.

Plasticizers are chemical compounds added to a base composition comprising one or more polymers with the purpose of lowering the glass transition temperature of the polymer composition, thereby making the composition more flexible and amenable to processing, e.g., by melt extrusion or molding. Plasticizers are typically used at various effective concentrations, and depending on the polymer used and desired properties of the compounded polymer formulations, plasticizers can be used at concentrations between 1 and 80% by weight of the unplasticized polymer. It is understood that, depending on the polymer and the plasticizer used, plasticizers can also confer other changes in physical and mechanical properties of the compounded polymer, as well as changes in barrier properties of the compounded polymer in respect to its permeability for various gases, water, water vapor, or organic compounds. It is also understood that one or more different plasticizers can be used in various blends with additional compounds for the preparation of an extrudable or moldable polymer composition. Such additional compounds can include various inorganic and organic filler compounds, wood dust, reinforcing fibers, dyes, pigments, stabilizers, lubricants, anti-microbial additives, and the like.

Plasticizers are typically mixed with a polymer by mixing at temperatures that are above or below the melting point of the polymer. Plasticizers can also be introduced with a help of an optional volatile solvent. Many variations of techniques for introducing plasticizer compounds to polymer compositions are known in the art.

The invention in other aspects is a composition comprising a compound or mixture of compounds of Structure I and a polymer. In one embodiment, the compound or mixture of compounds of Structure I is melt blended or solution blended with the polymer.

In one embodiment, the composition has a glass transition temperature at least 5° C., specifically, at least 10° C., more specifically at least 15° C., more specifically at least 20° C., more specifically at least 25° C., and even more specifically at least 30° C. lower than a glass transition temperature of the polymer.

In one embodiment, the compound or mixture of compounds of Structure I constitute from 0.1 to 90%, more specifically, from 0.5 to 80%, more specifically, from 1 to 70%, more specifically, from 5 to 65%, more specifically, from 5 to 60%, more specifically, from 10 to 50%, and more specifically, from 10 to 40% of the combined weight of the compound or mixture of compounds of Structure I and the polymer.

In one embodiment, the ratio by weight of polymer to the compound or mixture of compounds of Structure I is from 30:1 to 1:2.5.

In one embodiment, the polymer is an organic polymer. In another embodiment, the polymer is a biopolymer. In another embodiment, the polymer is a thermoplastic polymer. In another embodiment, the polymer is a thermoset polymer.

Poly(vinyl chloride) polymers, PVC, are homopolymers or co-polymers of vinyl chloride. Many PVC compounds of various degree of polymerization, cross-linking, and copolymer composition are known in the art and are produced industrially.

Poly(3-hydroxyalkanoates), PHA, are polyester homopolymers or co-polymers of 3-hydroxyalkanoic acids. Preferably, PHA is composed of linear 3-hydroxyalkanoic fragments having from 3 to 18 carbon atom atoms. Poly(3-hydroxybutyrate), PHB, is a homopolymer that is produced biologically, for example by various microorganisms. A pure PHB polymer is a brittle polymer having a narrow range of processing temperatures, and it decomposes readily at temperatures that are only 20-30° C. above its melting temperature.

Poly(lactate), or poly(lactide), PLA, is a known polyester homopolymer comprising repeat units of lactic acid of various stereochemistry.

Polysaccharides are homopolymers and co-polymers, linear or branched, comprising hexose or pentose fragments connected via glycosyl linkages. The polysaccharides may optionally contain various additional groups such as acylamido groups, sulfate ester groups, carboxylic ester groups, alkyl and hydroxyalkyl ether groups, and the like. Such additional groups may be present in polysaccharides derived from natural sources or can be artificially introduced (i.e., by acylation of cellulose). Examples of polysaccharides include acylated derivatives of cellulose and starch, as well as native or acylated chitin and pectin.

Some specific polymers that can be used include, poly(vinyl chloride)s, polyhydroxyalkanoates, poly(lactic acid)s, polystyrenes, polyurethanes, polyureas, polyurea-urethanes, polycarbonates, acrylic polymers, styrene-acrylic polymers, vinyl-acrylic polymers, ethylene-vinyl acetate polymers, polyesters, polyamides, chlorinated polyethylenes, polyethers, polybutadienes, acrylonitrile-butadiene-styrene copolymers, acrylonitrile butadiene copolymers, styrene-butadiene-styrene copolymers, methacrylate-butadiene-styrene copolymers, polyvinyl acetates, cellulose acetate polymers, cellulose acetate butyrate polymers, cellulose propionate polymers, elastomers, or homopolymers thereof, or random, graft, or block copolymers thereof, or blends or mixtures thereof. In a specific embodiment, the polymer is the polymer is a poly(vinyl chloride) homopolymer or copolymer. In another specific embodiment the polymer is a poly(lactic acid) homopolymer or copolymer.

In a specific embodiment, the polymer is a poly vinyl chloride material. In one embodiment, the polyvinyl chloride material has a K value in the range of from 65 to 75, more specifically, 65 to 70. In another embodiment, the polyvinyl chloride material has a K value above 70. In another embodiment, the polyvinyl chloride material has a K value in the range of 60 to 67.

In one embodiment, the invention is a PVC composition, including PVC and the compound or mixture of compounds of Structure I. In one embodiment, the composition has a content of from 5 to 250 parts by weight of the compound or mixture of compounds of Structure I per 100 parts by weight of PVC.

In one embodiment the composition is a plastics composition. In one embodiment, the plastics composition includes PVC. In another embodiment, the plastics composition includes polyalkyl methacrylate (PAMA). In another embodiment, the plastics composition includes polyvinyl acetate (PVAc). In another embodiment, the plastics composition includes polyvinyl butyral (PVB). In another embodiment, the plastics composition includes polylactic acid (PLA). In another embodiment, the plastics composition includes polyhydroxybutyric acid (PHB).

In one embodiment, the composition is a plastisol. The plastisol composition can be a dry blend or at least a portion of the compound or mixture of compounds of Structure I is in a liquid phase of the plastisol. When the plastisol is a dry blend, at least a portion of the compound or mixture of compounds of Structure I is absorbed or adsorbed into the polymer.

Plastisols in accordance with the invention are useful in the production of sheet stock or films, flooring, tents, tarpaulins, coated fabrics such as automobile upholstery, in car underbody coatings, in moldings and other consumer products. Plastisols are also used in medical uses such as blood bags and multilayered sheets and films, tubing, footwear, fabric coating, toys, flooring products and wallpaper. Plastisols typically contain 40 to 200 parts by weight, more typically 50 to 150 parts by weight, more typically 70 to 120 parts by weight, more typically 90 to 110 parts by weight of plasticizer per 100 parts of dispersed polymer particles. PVC plastisols are usually made from PVC that has been produced by emulsion polymerization.

In certain embodiments, compounds according to Structure I are contained in a PVC plastisol composition containing from 40 to 200 parts by weight, or 50 to 150 parts by weight, or 70 to 120 parts by weight, or 90 to 110 parts by weight of the compound per 100 parts of PVC. Such plastisol compositions tend to have stable viscosities; their viscosities tend to increase less than about 200% over a period of 14 days when stored at a temperature between about 20° C. to 25° C., or less than about 100%, preferably less than 70% and more preferably less than 50% when stored at a temperature of between about 20° C. to 25° C. for five days.

In one embodiment, the invention is a plastisol, including PVC and the compound or mixture of compounds of Structure I. In one embodiment the composition has a content of from 5 to 250 parts by weight of the compound or mixture of compounds of Structure I per 100 parts by weight of PVC.

In another embodiment of the present disclosure, a process for the production of flexible PVC articles is provided, whereby a layer is formed from a plastisol containing from 40 to 200 parts by weight, or 50 to 150 parts by weight, or 70 to 120 parts by weight, or 90 to 110 parts by weight of a plasticizer composition containing one or more compounds of Structure I per 100 parts by weight of PVC, and subsequently fusing the layer by the application of heat.

In some embodiments, the compositions of the invention described above include one or more additives, such as crosslinkers, adjuvants, colorants (dyes or pigments), anti-fouling agents (such as antifungal, antibacterial, or antiviral agents), tougheners, tackifiers, diluents, viscosity modifying agents, additional polymers, solvents, fillers, metal particulates, odor scavenging agents, lubricants, thermal stabilizers, light stabilizers including UV stabilizers, flame retardant additives, pigments, blowing agents, processing aids, impact modifiers, coalescing solvents, antioxidant or a combination of any two or more thereof. The additional materials impart various elements of functionality to the composition, the nature of which depend on the intended use of the composition, for example in one or more articles as will be described below.

The term "antioxidant" is recognized in the art and refers to a molecule capable of inhibiting the oxidation of other molecules. Oxidation is a chemical reaction that transfers electrons or hydrogen from a substance to an oxidizing agent. Oxidation reactions can produce free radicals. In turn, these radicals can start chain reactions which can degrade a material.

Suitable antioxidants include, for example, hindered phenols with an ester group, hindered phenol diamides, hindered phenols with an ether-ester linkage, hindered phenols with a hydrocarbyl ester linkage, hindered phenols, hindered amines, phosphites, alpha-beta unsaturated ketones, or mixtures thereof.

Exemplary antioxidant additives include organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite, alkylated monophenols or polyphenols; alkylated reaction products of polyphenols with dienes, such as tetrakis[methylene(3,5-di-tert-butyl-4-hydroxyhydrocinnamate)] methane; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl) propionate; amide of beta-(3,5-di-tert-butyl-4-hydroxyphenyl)-propionic acid, or combinations comprising at least one of the foregoing antioxidants. Antioxidants are generally used in amounts of 0.0001 to 5 parts by weight, based on 100 parts by weight of the composition.

Exemplary heat stabilizer additives include organophosphites such as triphenyl phosphite, tris-(2,6-dimethylphenyl) phosphite, tris-(mixed mono- and di-nonylphenyl)phosphite; phosphonates such as dimethylbenzene phosphonate, phosphates such as trimethyl phosphate, or combinations comprising at least one of the foregoing heat stabilizers. Heat stabilizers are generally used in amounts of 0.0001 to 5 parts by weight, based on 100 parts by weight of the composition.

Light stabilizers and/or ultraviolet light (UV) absorbing additives can also be used. Exemplary light stabilizer additives include benzotriazoles such as 2-(2-hydroxy-5-methylphenyl)benzotriazole, 2-(2-hydroxy-5-tert-octylphenyl)-benzotriazole and 2-hydroxy-4-n-octoxy benzophenone, or combinations comprising at least one of the foregoing light stabilizers. Light stabilizers are generally used in amounts of 0.0001 to 5 part by weight, based on 100 parts by weight of the plasticizer composition.

The term "UV absorber" (ultraviolet light absorber) is recognized in the art and is intended include molecules used in organic materials (polymers, paints, etc.) to absorb UV light to reduce the UV degradation (photo-oxidation) of a material. A number of different UVAs with different absorption properties exist. Examples include 2-hydroxyphenyl-benzophenone, a 2-(2-hydroxyphenyl)-benzotriazole, a 2-hydroxyphenyl-s-triazine), ethanediamide, N-(2-ethoxyphenyl)-N'-(2-ethylphenyl)- or mixtures thereof.

Exemplary UV absorbing additives include hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB® 5411); 2-hydroxy-4-n-octyloxybenzophenone (CYASORB® 531); 2-[4,6-bis(2,4-dimethylphenyl)-1,3,5-triazin-2yl]5-(octyloxy)-pheno-1 (CYASORB® 1164); 2,2'-(1,4-phenylene)bis(4H-3,1-benzoxazin-4-one) (CYASORB® UV-3638); 1,3-bis[(2-cyano-3,3-diphenylacryloyl) oxy]-2,2-bis[[(2-cyano-3, 3-diphenylacryloyl)oxy]methyl] propane (UVINUL® 3030); 2,2'-(1,4-phenylene) bis(4H-3,1-benzoxazin-4-one); 1,3-bis[(2-cyano-3,3-diphenylacryloyl)oxy]-2,2-bis[[(2-cyano-3,3-diphenyl-acryloyl)oxy]methyl]propane; nano-size inorganic materials such as titanium oxide, cerium oxide, and zinc oxide, all with particle size less than or equal to about 100 nanometers; or combinations comprising at least one of the foregoing UV absorbers. UV absorbers are generally used in amounts of 0.0001 to 10 parts by weight, based on 100 parts by weight of the composition.

Other suitable UV absorbers include, for example, benzophenones, such as CYASORB UV-9 (2-hydroxy-4-methoxybenzophenone, CHIMASSORB 81 (or CYASORB UV 531) (2 hydroxy-4 octyloxybenzophenone).

TINUVIN P, TINUVIN 234, TINUVIN 326, TINUVIN 328, CYASORB UV 5411 and CYASORB UV 237 are suitable examples of benzotriazoles.

CYASORB UV 1164 (2-[4,6-bis(2,4-dimethylphenyl)-1,3,5-triazin-2yl]-5(oxctyloxy) phenol is an exemplary triazine UV absorber. CYASORB 3638 is a suitable UV absorber which is a benzoxazinone.

In addition, hindered amine light stabilizers (HALS) are extremely efficient stabilizers against light-induced degradation of most polymers. They do not generally absorb UV radiation, but act to inhibit degradation of the polymer. These are typically tetra alkyl piperidines, such as 2,2,6,6-tetramethyl-4-piperidinamine and 2,2,6,6-tetramethyl-4-piperidinol.

The phrase "thermal stabilizer" is recognized in the art and refers to materials that prevent various effects such as oxidation, chain scission and uncontrolled recombinations and cross-linking reactions that are caused by oxidation of polymers.

Suitable examples of thermal stabilizers include Group I or Group II metal stearates, such as sodium or calcium stearate.

The compositions described herein include from about 0.01 to about 5.0 percent by weight of the total composition of an antioxidant, a UV stabilizer, a thermal stabilizer, or mixtures thereof. Exemplary amounts include 0.02, 0.05, 0.1, 0.2, 0.5, 1.0, 1.5, 2.0, and all amounts between 0.01 and 5.0.

In another aspect, the compositions described above include a blend of a compound of Structure I or a mixture of compounds of Structure I and at least one other plasticizer. The composition comprises from 20 to 200 parts, more specifically, 20 to 150 parts, more specifically, 20 to 100 parts, more specifically, 20 to 80 parts, and more specifically, 20 to 60 parts of the compound of any of Structure I and the at least one other plasticizer, per 100 parts of the polymer, specifically a polyvinyl chloride material (parts being by weight).

In one embodiment the blend includes from 95 wt % to 5 wt %, more specifically, 90 wt % to 10 wt %, more specifically, 80 wt % to 10 wt %, more specifically, 80 wt % to 20 wt %, more specifically, 70 wt % to 20 wt %, more specifically, 70 wt % to 30 wt %, more specifically, 60 wt % to 30 wt %, and more specifically, 60 wt % to 40 wt % of the compound of Structure I or a mixture of compounds of Structure I and from 5 wt % to 95 wt %, more specifically, 10 wt % to 90 wt %, more specifically, 20 wt % to 90 wt %, more specifically, 20 wt % to 80 wt %, more specifically, 30 wt % to 80 wt %, more specifically, 30 wt % to 70 wt %, more specifically, 40 wt % to 70 wt %, and more specifically, 40 wt % to 60 wt % of the at least one other plasticizer, based upon the total weight of the plasticizer present.

In another embodiment, the composition includes from 40 to 180 parts, more specifically, 50 to 160 parts, more specifically, 60 to 150 parts, more specifically, 70 to 120 parts, and more specifically, 70 to 100 parts, of the compound of Structure I and the at least one other plasticizer, per 100 parts of the polymer, specifically the polyvinyl chloride material (parts being by weight).

In another embodiment, the blend comprises at least 10%, more specifically, at least 15%, more specifically, at least 20%, more specifically, at least 25%, more specifically, at least 30%, more specifically, at least 35%, more specifically, at least 40%, more specifically, at least 45%, more specifically, at least 50%, more specifically, at least 55%, more specifically, at least 60%, more specifically, at least 65%, of the compound of or the mixture of compounds of Structure I, based upon the total weight of the plasticizer present.

In another embodiment, the compound of Structure I is present in the amount of 5 to 40 wt %, more specifically, 5 to 30%, more specifically, 10 to 25%, and more specifically, 10 to 20%, based on the weight of the total plasticizer. In another embodiment, the plasticizer composition contains from 15 to 90%, more specifically, from 15 to 80%, more specifically, from 20 to 80%, more specifically, from 30 to 60%, and more specifically, from 30 to 50%, by weight of the compound or mixture of compounds of Structure I, the remainder to 100% by weight being the portions by weight of all the plasticizers. In another embodiment, a molar ratio of the other plasticizer to the compound or mixture of compounds of Structure I is from 1:10 to 10:1.

The other plasticizer in the composition can be any plasticizer. In one embodiment, the other plasticizer is a cyclohexane dicarboxylic acid ester or a mixture of cyclohexane dicarboxylic acid esters. In one embodiment, the other plasticizer is not an ester of a cyclohexane carboxylic acid.

Some exemplary cyclohexane dicarboxylic acid esters include 1,2-cyclohexane dicarboxylic acid diisobutyl, 1,2-cyclohexane dicarboxylic acid dicyclohexyl, 1,2-cyclohexane dicarboxylic acid diisoheptyl, 1,2-cyclohexane dicarboxylic acid di (3,5,5-trimethyl hexyl), 1,2-cyclohexane dicarboxylic acid di (2,6-di methyl-4-heptyl), 1,2-cyclohexane dicarboxylic acid diisodecyl, 1,2-cyclohexane dicarboxylic acid diisoundecyl, 1,2-cyclohexane dicarboxylic acid diisotridecyl, 1,2-cyclohexane dicarboxylic acid di isononyl, 1,2-cyclohexane dicarboxylic acid di-2-ethylhexyl, 1,2-cyclohexane dicarboxylic acid di-2-propyl heptyl, 1,2-cyclohexane dicarboxylic acid diisooctadecyl, diisooctadecyl, 3-methyl-1,2-cyclohexane dicarboxylic acid diisobutyl, 3-methyl-1,2-cyclohexane dicarboxylic acid dicyclohexyl, 3-methyl-1,2-cyclohexane dicarboxylic acid diisoheptyl, 3-methyl-1,2-cyclohexane dicarboxylic acid di (2-ethylhexyl), 3-methyl-1,2-cyclohexane dicarboxylic acid di (3,5,5-trimethyl hexyl), 3-methyl-1,2-cyclohexane dicarboxylic acid di (2,6-di methyl-4-heptyl), 3-methyl-1,2-cyclohexane dicarboxylic acid diisodecyl, 3-methyl-1,2-cyclohexane dicarboxylic acid di isononyl, 3-methyl-1,2-cyclohexane dicarboxylic acid di-2-ethylhexyl, 3-methyl-1,2-cyclohexane dicarboxylic acid di-2-propyl heptyl, 3-methyl-1,2-cyclohexane dicarboxylic acid diisoundecyl, 3-methyl-1,2-cyclohexane dicarboxylic acid diisotridecyl, 3-methyl-1,2-cyclohexane dicarboxylic acid diisooctadecyl, 4-methyl-1,2-cyclohexane dicarboxylic acid diisobutyl, 4-methyl-1,2-cyclohexane dicarboxylic acid dicyclohexyl, 4-methyl-1,2-cyclohexane dicarboxylic acid diisoheptyl, 4-methyl-1,2-cyclohexane dicarboxylic acid di (3,5,5-trimethyl hexyl), 4-methyl-1,2-cyclohexane dicarboxylic acid di (2,6-di methyl-4-heptyl), 4-methyl-1,2-cyclohexane dicarboxylic acid diisodecyl, 4-methyl-1,2-cyclohexane dicarboxylic acid diisoundecyl, 4-methyl-1,2-cyclohexane dicarboxylic acid diisotridecyl, 4-methyl-1,2-cyclohexane dicarboxylic acid diisooctadecyl, 1,2-cyclohexane dicarboxylic acid di heptyl, 1,2-cyclohexane dicarboxylic acid dioctyl, 1,2-cyclohexane dicarboxylic acid di decyl, 1,2-cyclohexane dicarboxylic acid di undecyl, 1,2-cyclohexane dicarboxylic acid di dodecyl, 1,2-cyclohexane dicarboxylic acid di tetradecyl, 1,2-cyclohexane dicarboxylic acid dihexadecyl, 1,2-cyclohexane dicarboxylic acid dioctadecyl, 3-methyl-1,2-cyclohexane dicarboxylic acid di heptyl, 3-methyl-1,2-cyclohexane dicarboxylic acid dioctyl, 3-methyl-1,2-cyclohexane dicarboxylic acid di decyl, 3-methyl-1,2-cyclohexane dicarboxylic acid di undecyl, 3-methyl-1,2-cyclohexane dicarboxylic acid di dodecyl, 3-methyl-1,2-cyclohexane dicarboxylic acid di tetradecyl, 3-methyl-1,2-cyclohexane dicarboxylic acid dihexadecyl, 3-methyl-1,2-cyclohexane dicarboxylic acid dioctadecyl, 4-methyl-1,2-cyclohexane dicarboxylic acid di heptyl, 4-methyl-1,2-cyclohexane dicarboxylic acid dioctyl, 4-methyl-1,2-cyclohexane dicarboxylic acid di decyl, 4-methyl-1,2-cyclohexane dicarboxylic acid di undecyl, 4-methyl-1,2-cyclohexane dicarboxylic acid di dodecyl, 4-methyl-1,2-cyclohexane dicarboxylic acid di tetradecyl, 4-methyl-1,2-cyclohexane dicarboxylic acid dihexadecyl, 4-methyl-1,2-cyclohexane dicarboxylic acid dioctadecyl, 1,2-cyclohexane dicarboxylic acid di heptyl, 1,2-cyclohexane dicarboxylic acid dioctyl, 1,2-cyclohexane dicarboxylic acid di decyl, 1,2-cyclohexane dicarboxylic acid di undecyl, 1,2-cyclohexane dicarboxylic acid di dodecyl, 1,2-cyclohexane dicarboxylic acid di tetradecyl, 1,2-cyclohexane dicarboxylic acid dihexadecyl, 1,2-cyclohexane dicarboxylic acid dioctadecyl, 3-methyl-1,2-cyclohexane dicarboxylic acid di heptyl, 3-methyl-1,2-cyclohexane dicarboxylic acid dioctyl, 3-methyl-1,2-cyclohexane dicarboxylic acid di decyl, 3-methyl-1,2-cyclohexane dicarboxylic acid di undecyl, 3-methyl-1,2-cyclohexane dicarboxylic acid di dodecyl, 3-methyl-1,2-cyclohexane dicarboxylic acid di tetradecyl, 3-methyl-1,2-cyclohexane dicarboxylic acid dihexadecyl, 3-methyl-1,2-cyclohexane dicarboxylic acid dioctadecyl, 4-methyl-1,2-cyclohexane dicarboxylic acid di heptyl, 4-methyl-1,2-cyclohexane dicarboxylic acid dioctyl, 4-methyl-1,2-cyclohexane dicarboxylic acid di decyl, 4-methyl-1,2-cyclohexane dicarboxylic acid di undecyl, 4-methyl-1,2-cyclohexane dicarboxylic acid di dodecyl, 4-methyl-1,2-cyclohexane dicarboxylic acid di tetradecyl, 4-methyl-1,2-cyclohexane dicarboxylic acid dihexadecyl, 4-methyl-1,2-cyclohexane dicarboxylic acid dioctadecyl, cyclohexane-1,2-dicarboxylic acid di(isopentyl) ester, obtainable by hydrogenation of a di(isopentyl)phthalate having the Chemical Abstracts registry number (in the following: CAS No.) 84777-06-0; cyclohexane-1,2-dicarboxylic acid di(isoheptyl) ester, obtainable by hydrogenating the di(isoheptyl)phthalate having the CAS No. 71888-89-6; cyclohexane-1,2-dicarboxylic acid di(isononyl) ester, obtainable by hydrogenating the di(isononyl)phthalate having the CAS No. 68515-48-0; cyclohexane-1,2-dicarboxylic acid di(isononyl) ester, obtainable by hydrogenating the di(isononyl)phthalate having the CAS No. 28553-12-0, which is based on n-butene; cyclohexane-1,2-dicarboxylic acid di(isononyl) ester, obtainable by hydrogenating the di(isononyl)phthalate having the CAS No. 28553-12-0, which is based on isobutene; a 1,2-di-C9-ester of cyclohexane dicarboxylic acid, obtainable by hydrogenating the di(nonyl)phthalate having the CAS No. 68515-46-8; cyclohexane-1,2-dicarboxylic acid di(isodecyl) ester, obtainable by hydrogenating a di(isodecyl)phthalate having the CAS No. 68515-49-1; 1,2-C7-11-ester of cyclohexane dicarboxylic acid, obtainable by hydrogenating the corresponding phthalic acid ester having the CAS No. 68515-42-4; 1,2-di-C7-11-ester of cyclohexane dicarboxylic acid, obtainable by hydrogenating the di-C7-11-phthalates having the following CAS Nos.: 111381-89-6, 111381-90-9, 111381-91-0, 68515-44-6, 68515-45-7 and 3648-20-7; a 1,2-di-C9-11-ester of cyclohexane dicarboxylic acid, obtainable by hydrogenating a di-C9-11-phthalate having the CAS No. 98515-43-5; a 1,2-di(isodecyl)cyclohexane dicarboxylic acid ester, obtainable by hydrogenating a di(isodecyl)phthalate, consisting essentially of di-(2-propylheptyl)phthalate; 1,2-di-C7-9-cyclohexane dicarboxylic acid ester, obtainable by hydrogenating the corresponding phthalic acid ester, which comprises branched and linear C7-9-alkylester groups; respective phthalic acid esters which may be used as starting materials have the following CAS Nos.: di-C7-9-alkylphthalate having the CAS No. 111 381-89-6; di-C7-alkylphthalate having the CAS No. 68515-44-6; and di-C9-alkylphthalate having the CAS No. 68515-45-7, as well as hydrogenated terephthalates.

Other exemplary plasticizers include diesters made from cyclohexanoic dicarboxylic acid and a mixture of alcohols having an average carbon number between 8.5 and 9.5.

In another embodiment, the other plasticizer is selected from adipate esters, citrate esters, succinate esters, phthalate esters, trimellitate esters, and polymeric esters, specifically, trimellitate esters.

Other exemplary plasticizers also include monomethyl terephthalate, dimethyl terephthalate, diethyl terephthalate, di-n-propyl terephthalate, di-n-butyl terephthalate, di-tert-butyl terephthalate, diisobutyl terephthalate, benzyl butyl terephthalate, di-(2-propyl-heptyl) terephthalate monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, di-n-octadecyl terephthalate, diisooctadecyl terephthalate, di-n-eicosyl terephthalate, monocyclohexyl terephthalate, dicyclohexyl terephthalate, monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate; alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-octadecyl isophthalate, diisooctadecyl isophthalate, di-n-eicosyl isophthalate, monocyclohexyl isophthalate, and dicyclohexyl isophthalate.

In another embodiment, the at least one other plasticizer is one of di-(2-ethylhexyl) adipate and diisononyl adipate.

In another embodiment, the at least one other plasticizer is one of diethylene glycol dibenzoate, butyl benzyl phthalate, dipropylene glycol dibenzoate, phenyl cresyl esters of pentadecyl sulfonic aromatic sulfonic acid esters, tributylacetyl citrate, tri-2-ethylhexyl phosphate, trioctyl phosphate, 2-ethylhexyl-isodecyl phosphate, di-2-ethylhexyl phenyl phosphate, triphenyl phosphate, and tricresyl phosphate.

In another embodiment, the at least one other plasticizer is a ketal. Exemplary ketals that can be used are disclosed in WO/2010/151558, entitled "Ketal compounds and Uses thereof," the disclosure which is hereby incorporated by reference in its entirety.

In another embodiment, the at least one other plasticizer is selected from terephthalate esters, dibenzoate esters, alkyl esters of aromatic tri- or tetra-carboxylic acids, ketal esters and aliphatic dicarboxylic acid esters with monohydric alcohols having 3 to 12 carbon atoms.

In another embodiment the other plasticizer is an alkyl ester of an aromatic polycarboxylic acid, an alkyl ester of a cyclohexanepolycarboxylic acid, an alkyl ester of benzoic acid, an alkyl ester of adipic acid, a dibenzoic ester of a diethylene glycol, a dibenzoic ester of a dipropylene glycol, a dibenzoic ester of a triethylene glycol, a dibenzoic ester of a tripropylene glycol, and a citric ester.

In another embodiment, the at least one other plasticizer is an ortho phthalate compound. In one embodiment, the ortho phthalate has the structure:

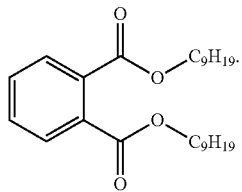

In another embodiment, the ortho phthalate has the structure

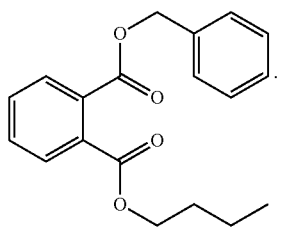 [SMILES: CCCCOC(=O)c1ccccc1C(=O)OCc1ccccc1]

In another embodiment, the at least one other plasticizer is a terephthalate compound. In one embodiment, the terephthalate compound has the structure

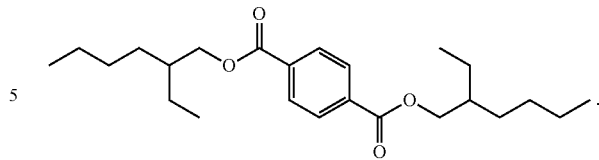

In another embodiment, the at least one other plasticizer is a benzoate ester compound. In one embodiment, the benzoate ester has the structure

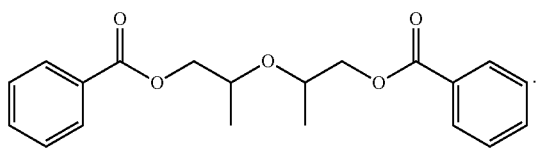 [SMILES: CC(COC(=O)c1ccccc1)OC(C)COC(=O)c1ccccc1]

In another embodiment, the at least one other plasticizer is a cycloaliphatic compound. In one embodiment, the cycloaliphatic compound has the structure corresponding to Structure III:

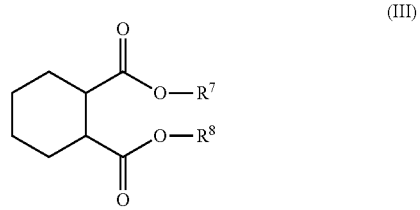

(III)

wherein $R^7$ and $R^8$ are each independently an optionally substituted linear or branched alkyl each having between 6 and 10 carbon atoms. In one embodiment, the cycloaliphatic compound is selected from the group consisting of:

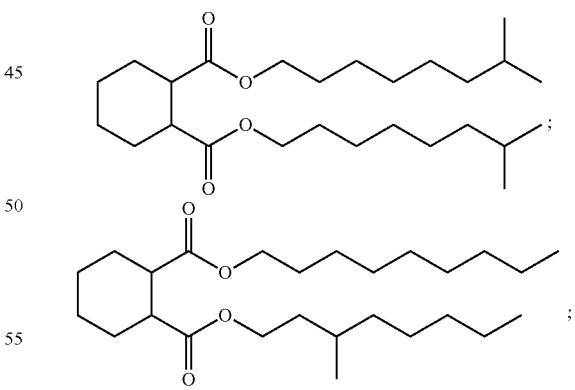

and combinations thereof.

A plastisol in accordance with the invention may further contain one or more additional plasticizers such as diethylene glycol dibenzoate, butyl benzyl phthalate, dibutyl phthalate, diisononyl phthalate, diisodecyl phthalate, other dialkyl phthalates, dipropylene glycol dibenzoate, such as the phenyl cresyl esters of pentadecyl sulfonic aromatic sulfonic acid esters available from Bayer AG of Leverkusen, Germany as MESAMOLL™, citrates such as tributylacetyl citrate, tri-2-ethylhexyl phosphate, trioctyl phosphate such as 2-ethylhexyl-isodecyl phosphate, di-2-ethylhexyl phenyl phosphate, biphenyl phosphate and tricresyl phosphate and the like.

Polymer compositions of the invention are useful to form a variety of articles. An "article" as used herein is an item with a discrete shape, such as a tube, a film, a sheet, or a fiber, that incorporates one or more compositions of the disclosure; in some embodiments, the article may have its origin in a composition that undergoes a transformation, such as solidification or evaporation of one or more solvents, to result in the final article. In some embodiments, an article is substantially formed from a polymer composition of the invention; in other embodiments, the polymer composition of the invention forms only one part, such as one layer, of an article.

An article can be formed from a polymer composition of the invention by a wide range of fabrication methods, including for example, coating, casting, extrusion, coextrusion, profile extrusion, blow molding, thermoforming, injection molding, coinjection molding, reaction injection molding, milling, or weaving. Where the polymer includes PVC, for example, the article is, in some embodiments, a casing, a pipe, a cable, a wire sheathing, a fiber, a woven fabric, a nonwoven fabric, a film, a window profile, a floor covering, a wall base, an automotive item, a medical item, a toy, a packaging container, a screw closure or stopper adapted for a bottle, a gasket, a sealing compound, a film, a synthetic leather item, an adhesive tape backing, or an item of clothing. In some embodiments, the casing is a casing for an electrical device. In some embodiments, the medical item is medical tubing or a medical bag. In some embodiments, the film is a roofing film, a composite film, a film for laminated safety glass, or a packaging film. In some embodiments, the packaging container is a food or drink container. In some embodiments, the sealing compound is for sealed glazing. In some embodiments, the automotive item is seat upholstery, an instrument panel, an arm rest, a head support, a gear shift dust cover, a seat spline, a sound-deadening panel, a window seal, a landau top, a sealant, a truck tarpaulin, a door panel, a cover for a console and glove compartment, a trim laminating film, a floor mat, a wire insulation, a side body molding, an underbody coating, a grommet, or a gasket.

In some embodiments, the article comprises two or more layers and the compound of any of Structure I constitutes or is contained within at least one layer. In another embodiment, the article comprises a composition containing one or more compound of Structure I in at least one layer. In some such embodiments, the other of the two adjacent layers contains a plasticizer that doesn't have a structure corresponding to Structure I, such as those described above. Some examples include, in various embodiments, dialkyl phthalates, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, epoxidized soybean oil, and mixtures thereof.

Certain polymer compositions in accordance with the invention are useful as adhesives, including as adhesive films or adhesive coatings. Such adhesives may include, for example, a poly(vinyl acetate) or vinyl acetate copolymer emulsion.

In some embodiments, the compounds of Structure I are useful as plasticizers in nail polish formulations. Polymers useful in nail polish formulations include nitrocellulose, tosylamide-formaldehydes and the like.

In one embodiment, the article is selected from coverings, window shades, films, sheetings, upholstery, synthetic leather, shoe soles, shoes, materials used for food contact, adhesive tapes, shoe and automobile interiors, stationary, wires, and cables.

In another embodiment, the article is selected from blood bags and medical tubing.

In another embodiment, the article is selected from coverings, window shades, films, sheetings, upholstery, synthetic leather, coated cloths and fabrics, toys, shoe soles, shoes, materials used for food contact, adhesive tapes, shoe and automobile interiors, car underbody coatings, wallpaper, stationary, and bottle caps.

In another embodiment, the article is a wire and cable coating. The article can include PVC and a compound of Structure I.

In another embodiment, the article is a car having an interior part comprising PVC and a plasticizer of Structure I.

In another embodiment, the article is a film produced from a plastisol comprising PVC and a plasticizer of Structure I.

In another embodiment, the article is a multilayer article in which at least two adjacent layers include plasticized polyvinyl chloride wherein the plasticizer in one of the two adjacent layers contains a compound of Structure I.

In one embodiment, the articles include a di-isononyl cyclohexanoate ester, a phthalate ester, a terephthalate ester, an adipate ester, a succinate ester, a citrate ester, a benzoate, di-2-ethyl hexyl phthalate, a cyclohexane dicarboxylic acid, or a cyclohexane polycarboxylic acid ester.

In another embodiment, the articles include at least one compound selected from the group consisting of terephthalate esters, dibenzoate esters, alkyl esters of aromatic tri- or tetra-carboxylic acids, ketal esters and aliphatic dicarboxylic acid esters with monohydric alcohols having 3 to 12 carbon atoms.

In one embodiment the articles are produced from a plastisol, specifically a PVC plastisol, including a compound of Structure I, wherein the plastisol is processed through plastisol coating of substrates, dipping, spraying, spreading, rotational molded, casting, or pouring to form the article.

In one embodiment, the invention is a paint, an ink, a coating, a plastisol, an adhesive, a component of an adhesive, a sealing composition, a plasticizer in a plastic, a plasticizer in a component of a plastic, a solvent, a component of a lubricating oil, or an auxiliary during metalworking, including a compound or mixture of compounds of Structure I.

In another embodiment, a finished article is made by a process including a step selected from extruding, moulding, and calendering.

The following paragraphs also provide for further still additional aspects of the present invention. In one embodiment, in a first paragraph (1), the invention is directed to a compound having a structure corresponding to structure I:

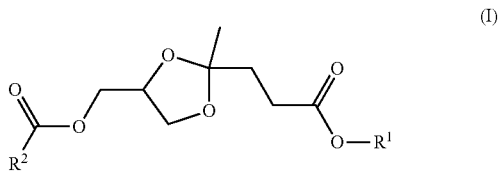

wherein:

R¹ is a linear, branched, or cyclic alkyl or aryl group comprising 2 to 18 carbon atoms and no oxygen atoms; and R² is a linear, branched, or cyclic alkyl or aryl group comprising 1 to 17 carbon atoms and no oxygen atoms.

2. The compound of paragraph 1, wherein R¹ comprises 2 to 4 carbon atoms.

3. The compound of paragraph 1, wherein R¹ comprises 8 to 12 carbon atoms.

4. The compound of paragraph 1, wherein R¹ comprises 14 to 18 carbon atoms.

5. The compound of paragraph 3, wherein R¹ comprises 8 carbon atoms.

6. The compound of paragraph 3, wherein R¹ comprises 9 carbon atoms.

8. The compound of paragraph 3, wherein R¹ comprises 10 carbon atoms.

9. The compound of paragraph 3, wherein R¹ comprises 12 carbon atoms.

10. The compound of any of paragraphs 1 through 9, wherein R² comprises 1 carbon atoms.

11. The compound of any of paragraphs 1 through 9, wherein R² comprises 5 carbon atoms.

12. The compound of any of paragraphs 1 through 9, wherein R² comprises 7 carbon atoms.

13. The compound of any of paragraphs 1 through 9, wherein R² comprises 9 carbon atoms.

14. The compound of any of paragraphs 1 through 9, wherein R² comprises 11 carbon atoms.

15. The compound of any of paragraphs 1 through 9, wherein R² comprises 13-17 carbon atoms.

16. The compound of any of paragraphs 1 through 9, wherein R² is an aryl group.

17. The compound of paragraph 1, having a structure corresponding to structure Ia:

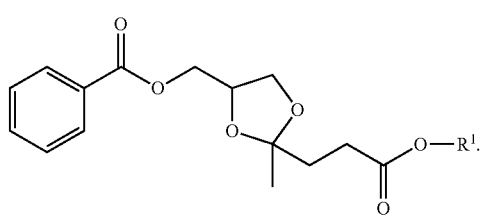

(Ia)

18. The compound of paragraph 17, wherein Structure (Ia) is selected from the group consisting of:

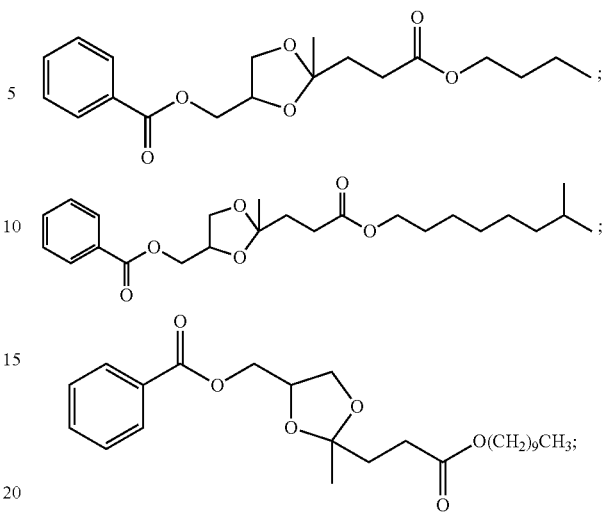

and mixtures thereof.

19. The compound of paragraph 1, having the structure:

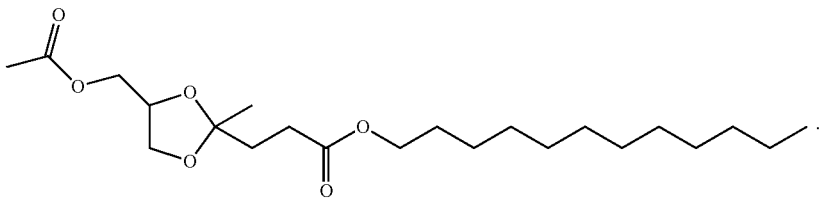 [SMILES: CCCCCCCCCCCCOC(=O)CCC1(C)OCC(COC(C)=O)O1]

20. The compound of paragraph 1, having the structure:

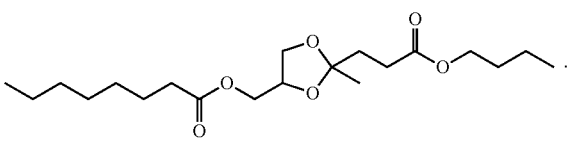 [SMILES: CCCCCCCC(=O)OCC1COC(C)(CCC(=O)OCCCC)O1]

21. The compound of paragraph 1, having the structure:

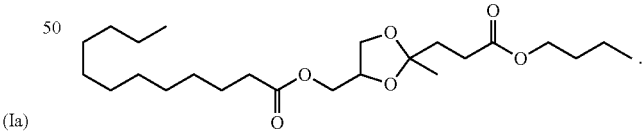

22. The compound of paragraph 1, having the structure:

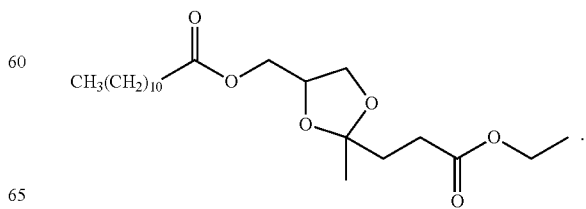

23. The compound of paragraph 1, having the structure:

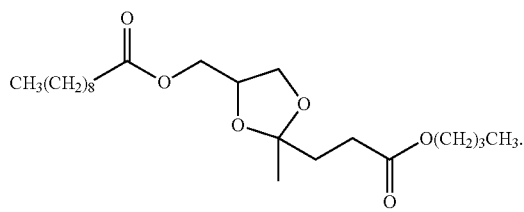

24. The compound of paragraph 1, having the structure:

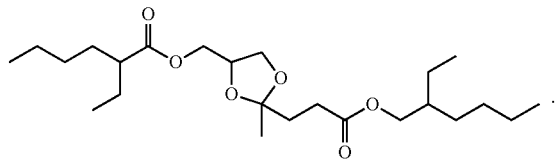 [SMILES: CCCCC(CC)COC(=O)CCC1(C)OCC(COC(=O)C(CC)CCCC)O1]

25. The compound of paragraph 1, having the structure:

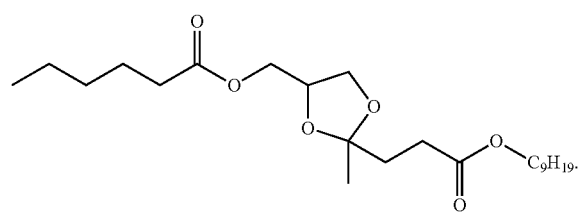

26. The compound of paragraph 1, wherein $R^2$ is a benzyl and $R^1$ comprises 12 carbon atoms.

27. The compound of paragraph 1, wherein Structure I is selected from the group consisting of:

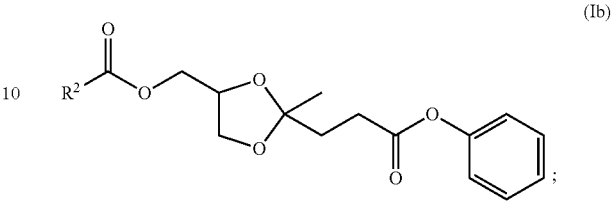

and combinations thereof.

28. The compound of paragraph 1, having the structure

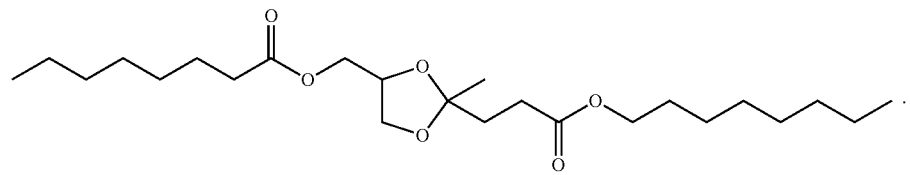 [SMILES: CCCCCCCCOC(=O)CCC1(C)OCC(COC(=O)CCCCCCC)O1]

29. The compound of paragraph 1, having the structure

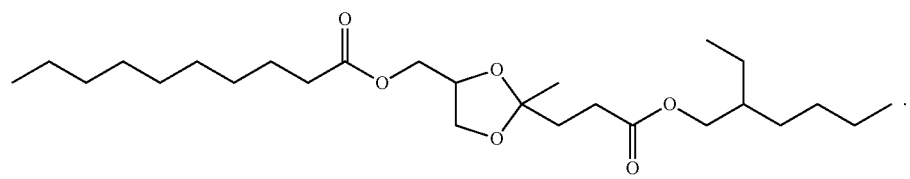 [SMILES: CCCCCCCCCC(=O)OCC1COC(C)(CCC(=O)OCC(CC)CCCC)O1]

30. The compound of paragraph 1, having the structure:

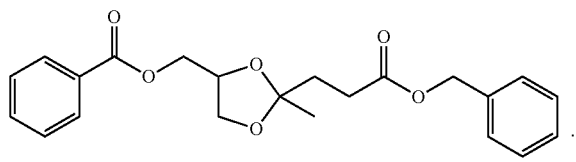 [SMILES: CC1(CCC(=O)OCc2ccccc2)OCC(COC(=O)c2ccccc2)O1]

31. The compound of paragraph 1, having the structure:

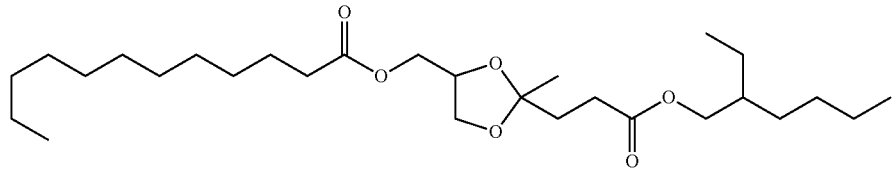

32. The compound of paragraph 1, having the structure:

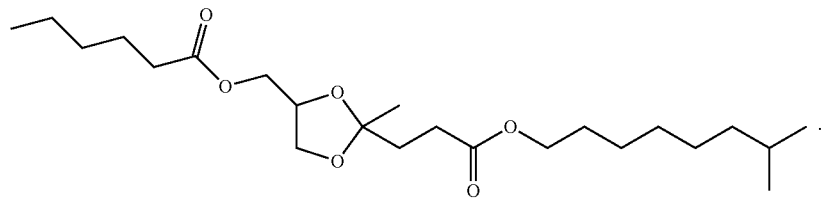 [SMILES: CCCCCC(=O)OCC1COC(C)(CCC(=O)OCCCCCCC(C)C)O1]

33. The compound of paragraph 1, having the structure:

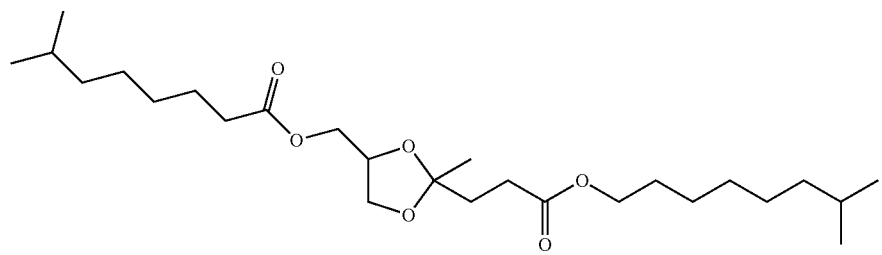

34. The compound of paragraph 1, having the structure:

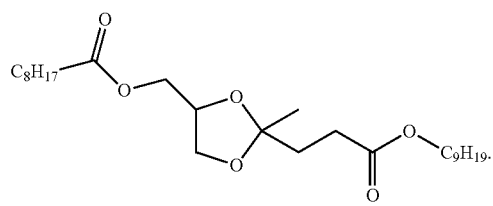

In one embodiment, in a thirty fifth paragraph (35), the invention is directed to a mixture comprising two or more compounds of any of paragraphs 1 through 34 (noted as [0439] through [0164]).

In one embodiment, in a thirty sixth paragraph (36), the invention is directed to a plasticizer composition comprising a compound of any of paragraphs 1 through 34 (noted as through [0164]).

The following paragraphs also provide for further still additional aspects of the present invention. In one embodiment, in a thirty seventh paragraph (37), the invention is directed to a composition comprising:

(a) a polymer; and
(b) a compound or mixture of compounds of any of paragraphs 1 through 34 (noted as through [0164]).

38. The composition of paragraph 37, which has a glass transition temperature at least 5° C. lower, specifically at least 30° C. lower than a glass transition temperature of the polymer.

39. The composition of paragraph 37, wherein the compound or mixture of compounds of any of claims 1 through 30 constitutes from 0.1 to 90% of the combined weight of the compound or mixture and the polymer.

40. The composition of paragraph 37, wherein the polymer is an organic polymer or a biopolymer.

41. The composition of paragraph 37, wherein the polymer is a thermoplastic or a thermoset.

42. The composition of paragraph 37, wherein the polymer comprises a poly(vinyl chloride), polyhydroxyalkanoate, a poly(lactic acid), a polystyrene, a polyurethane, a polyurea, a polyurea-urethane, a polycarbonate, an acrylic polymer, a styrene-acrylic polymer, a vinyl-acrylic polymer, an ethylene-vinyl acetate polymer, a polyester, a polyamide, a chlorinated polyethylene, a polyether, a polybutadiene, an acrylonitrile-butadiene-styrene copolymer, an acrylonitrile butadiene copolymer, a styrene-butadiene-styrene copolymer, a methacrylate-butadiene-styrene copolymer, a polyvinyl acetate, a cellulose acetate polymer, a cellulose acetate butyrate polymer, a cellulose propionate polymer, an elastomer, or homopolymers thereof, or random, graft, or block copolymers thereof, or blends or mixtures thereof.

43. The composition of paragraph 37, wherein the polymer is a poly(vinyl chloride) homopolymer or copolymer.

44. The composition of paragraph 37, wherein the polymer is a poly(lactic acid) homopolymer or copolymer.

45. The composition of paragraph 37, wherein the compound or mixture of compounds of any of claims 1 through 30 is melt blended or solution blended with the polymer.

46. The composition of paragraph 37, wherein the composition is a plastisol.

47. The composition of paragraph 46, wherein at least a portion of the compound or mixture of compounds of any of claims 1 through 34 is in a liquid phase of the plastisol.

48. The composition of paragraph 46, wherein the composition is a dry blend.

49. The composition of paragraph 48, wherein at least a portion of the compound or mixture of compounds is absorbed into the polymer.

50. The composition of paragraph 48, wherein at least a portion of the compound or mixture of compounds is adsorbed into the polymer.

51. The composition of any of paragraphs 37 through 50, further comprising one or more crosslinkers, adjuvants, colorants, antifouling agents, tougheners, solvents, fillers, metal particulates, odor scavenging agents, lubricants, thermal stabilizers, light stabilizers including UV stabilizers, flame retardant additives, pigments, blowing agents, processing aids, impact modifiers, coalescing solvents, antioxidant or a combination of any two or more thereof.

52. The composition of any of paragraphs 37 through 50, further comprising one or more additives selected from the group consisting of terephthalates, phthalates, benzoates, aliphatic esters (such as adipates, succinates, citrates and azaleates), dialkyl phthalates, trimethyl pentanyl diisobutyrate, dialkyl isophthalates, dialkyl terephthalates, alkyl benzyl phthalates, alkyl benzyl terephthalates, dibenzyl phthalates, dibenzyl terephthalates, dialkyl adipates, dialkyl succinates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, monobenzoates, dibenzoates, tribenzoates, epoxidized seed oils (such as epoxidized soybean oil or epoxidized linseed oil), chlorinated paraffins, diglycerides, triglycerides, polyketals, polymeric plasticizers and mixtures thereof.

In one embodiment, in a fifty third paragraph (53), the invention is directed to an article comprising the composition of any of paragraphs 37 through 52 (noted as [0166] through [0181]).

The following paragraphs also provide for further still additional aspects of the present invention. In one embodiment, in a fifty fourth paragraph (54), the invention is directed to a composition comprising the product of;
(a) a polyvinyl chloride material; and
(b) a blend comprising a compound of any of paragraphs 1 through 34 or a mixture of compounds of any of paragraphs 1 through 34 (noted as [0439] through [0164]) and at least one other plasticizer; wherein the composition comprises from 20 to 200 parts of the compound of any of paragraphs 1 through 34 and the at least one other plasticizer, per 100 parts of the polyvinyl chloride material (parts being by weight).

55. The composition of paragraph 54, wherein the blend comprises from 90 wt % to 10 wt % of the compound of any of claims 1 through 34 or a mixture of compounds of any of claims 1 through 34 and from 10 wt % to 90 wt % of the at least one other plasticizer, based upon the total weight of the plasticizer present.

56. The composition of paragraph 54, wherein the blend comprises from 95 wt % to 5 wt % of the compound of any of claims 1 through 34 or a mixture of compounds of any of claims 1 through 34 and from 5 wt % to 95 wt % of the at least one other plasticizer, based upon the total weight of the plasticizer present.

57. The composition of any of paragraphs 54 through 56, wherein the other plasticizer is a cyclohexane dicarboxylic acid ester or a mixture of cyclohexane dicarboxylic acid esters.

58. The composition of paragraph 57, wherein the cyclohexane dicarboxylic acid ester is selected from the group consisting of or the mixture comprises at least one of 1,2-cyclohexane dicarboxylic acid diisobutyl, 1,2-cyclohexane dicarboxylic acid dicyclohexyl, 1,2-cyclohexane dicarboxylic acid diisoheptyl, 1,2-cyclohexane dicarboxylic acid di (3,5,5-trimethyl hexyl), 1,2-cyclohexane dicarboxylic acid di (2,6-di methyl-4-heptyl), 1,2-cyclohexane dicarboxylic acid diisodecyl, 1,2-cyclohexane dicarboxylic acid diisoundecyl, 1,2-cyclohexane dicarboxylic acid diisotridecyl, 1,2-cyclohexane dicarboxylic acid di isononyl, 1,2-cyclohexane dicarboxylic acid di-2-ethylhexyl, 1,2-cyclohexane dicarboxylic acid di-2-propyl heptyl, 1,2-cyclohexane dicarboxylic acid diisooctadecyl, diisooctadecyl, 3-methyl-1,2-cyclohexane dicarboxylic acid diisobutyl, 3-methyl-1,2-cyclohexane dicarboxylic acid dicyclohexyl, 3-methyl-1,2-cyclohexane dicarboxylic acid diisoheptyl, 3-methyl-1,2-cyclohexane dicarboxylic acid di (2-ethylhexyl), 3-methyl-1,2-cyclohexane dicarboxylic acid di (3,5,5-trimethyl hexyl), 3-methyl-1,2-cyclohexane dicarboxylic acid di (2,6-di methyl-4-heptyl), 3-methyl-1,2-cyclohexane dicarboxylic acid diisodecyl, 3-methyl-1,2-cyclohexane dicarboxylic acid di isononyl, 3-methyl-1,2-cyclohexane dicarboxylic acid di-2-ethylhexyl, 3-methyl-1,2-cyclohexane dicarboxylic acid di-2-propyl heptyl, 3-methyl-1,2-cyclohexane dicarboxylic acid diisoundecyl, 3-methyl-1,2-cyclohexane dicarboxylic acid diisotridecyl, 3-methyl-1,2-cyclohexane dicarboxylic acid diisooctadecyl, 4-methyl-1,2-cyclohexane dicarboxylic acid diisobutyl, 4-methyl-1,2-cyclohexane dicarboxylic acid dicyclohexyl, 4-methyl-1,2-cyclohexane dicarboxylic acid diisoheptyl, 4-methyl-1,2-cyclohexane dicarboxylic acid di (3,5,5-trimethyl hexyl), 4-methyl-1,2-cyclohexane dicarboxylic acid di (2,6-di methyl-4-heptyl), 4-methyl-1,2-cyclohexane dicarboxylic acid diisodecyl, 4-methyl-1,2-cyclohexane dicarboxylic acid diisoundecyl, 4-methyl-1,2-cyclohexane dicarboxylic acid diisotridecyl, and 4-methyl-1,2-cyclohexane dicarboxylic acid diisooctadecyl.

59. The composition of paragraph 57, wherein the cyclohexane dicarboxylic acid ester is selected from the group consisting of or the mixture comprises at least one of 1,2-cyclohexane dicarboxylic acid di heptyl, 1,2-cyclohexane dicarboxylic acid dioctyl, 1,2-cyclohexane dicarboxylic acid di decyl, 1,2-cyclohexane dicarboxylic acid di undecyl, 1,2-cyclohexane dicarboxylic acid di dodecyl, 1,2-cyclohexane dicarboxylic acid di tetradecyl, 1,2-cyclohexane dicarboxylic acid dihexadecyl, 1,2-cyclohexane dicarboxylic acid dioctadecyl, 3-methyl-1,2-cyclohexane dicarboxylic acid di heptyl, 3-methyl-1,2-cyclohexane dicarboxylic acid dioctyl, 3-methyl-1,2-cyclohexane dicarboxylic acid di decyl, 3-methyl-1,2-cyclohexane dicarboxylic acid di undecyl, 3-methyl-1,2-cyclohexane dicarboxylic acid di dodecyl, 3-methyl-1,2-cyclohexane dicarboxylic acid di tetradecyl, 3-methyl-1,2-cyclohexane dicarboxylic acid dihexadecyl, 3-methyl-1,2-cyclohexane dicarboxylic acid dioctadecyl, 4-methyl-1,2-cyclohexane dicarboxylic acid di heptyl, 4-methyl-1,2-cyclohexane dicarboxylic acid dioctyl, 4-methyl-1,2-cyclohexane dicarboxylic acid di decyl, 4-methyl-1,2-cyclohexane dicarboxylic acid di undecyl, 4-methyl-1,2-cyclohexane dicarboxylic acid di dodecyl, 4-methyl-1,2-cyclohexane dicarboxylic acid di tetradecyl, 4-methyl-1,2-cyclohexane dicarboxylic acid dihexadecyl, and 4-methyl-1,2-cyclohexane dicarboxylic acid dioctadecyl.

60. The composition of paragraph 57, wherein the cyclohexane dicarboxylic acid ester is selected from the group consisting of or the mixture comprises at least one of cyclohexane-1,2-dicarboxylic acid di(isopentyl) ester, obtainable by hydrogenation of a di(isopentyl)phthalate having the Chemical Abstracts registry number (in the following: CAS No.) 84777-06-0; cyclohexane-1,2-dicarboxylic acid di(isoheptyl) ester, obtainable by hydrogenating the di(isoheptyl)phthalate having the CAS No. 71888-89-6; cyclohexane-1,2-dicarboxylic acid di(isononyl) ester, obtainable by hydrogenating the di(isononyl)phthalate having the CAS No. 68515-48-0; cyclohexane-1,2-dicarboxylic acid di(isononyl) ester, obtainable by hydrogenating the di(isononyl)phthalate having the CAS No. 28553-12-0, which is based on n-butene; cyclohexane-1,2-dicarboxylic acid di(isononyl) ester, obtainable by hydrogenating the di(isononyl)phthalate having the CAS No. 28553-12-0, which is based on isobutene; a 1,2-di-C9-ester of cyclohexane dicarboxylic acid, obtainable by hydrogenating the di(nonyl)phthalate having the CAS No. 68515-46-8; cyclohexane-1,2-dicarboxylic acid di(isodecyl) ester, obtainable by hydrogenating a di(isodecyl)phthalate having the CAS No. 68515-49-1; 1,2-C7-11-ester of cyclohexane dicarboxylic acid, obtainable by hydrogenating the corresponding phthalic acid ester having the CAS No. 68515-42-4; 1,2-di-C7-11-ester of cyclohexane dicarboxylic acid, obtainable by hydrogenating the di-C7-11-phthalates having the following CAS Nos.: 111381-89-6, 111381-90-9, 111381-91-0, 68515-44-6, 68515-45-7 and 3648-20-7; a 1,2-di-C9-11-ester of cyclohexane dicarboxylic acid, obtainable by hydrogenating a di-C9-11-phthalate having the CAS No. 98515-43-5; a 1,2-di(isodecyl)cyclohexane dicarboxylic acid ester, obtainable by hydrogenating a di(isodecyl)phthalate, consisting essentially of di-(2-propylheptyl)phthalate; 1,2-di-C7-9-cyclohexane dicarboxylic acid ester, obtainable by hydrogenating the corresponding phthalic acid ester, which comprises branched and linear C7-9-alkylester groups; respective phthalic acid esters which may be used as starting materials have the following CAS Nos.: di-C7-9-alkylphthalate having the CAS No. 111 381-89-6; di-C7-alkylphthalate having the CAS No. 68515-44-6; and di-C9-alkylphthalate having the CAS No. 68515-45-7.

61. The composition of paragraph 57, wherein the mixture comprises diesters made from cyclohexanoic dicarboxylic acid and a mixture of alcohols having an average carbon number between 8.5 and 9.5.

62. The composition any of paragraphs 54 through 56, wherein the blend comprises from 30 to 60 wt % of the compound of any of claims 1 through 34 or a mixture of compounds of any of claims 1 through 34, based upon the total weight of the plasticizer present.

63. The composition any of paragraphs 54 through 56, wherein the at least one other plasticizer is selected from the group consisting of at least one of adipate esters, citrate esters, succinate esters, phthalate esters, trimellitate esters, and polymeric esters.

64. The composition of any of paragraphs 54 through 56, wherein the at least one other plasticizer is a trimellitate ester.

65. The composition of any of paragraphs 54 through 56, wherein the at least one other plasticizer is selected from the group consisting of at least one of monomethyl terephthalate, dimethyl terephthalate, diethyl terephthalate, di-n-propyl terephthalate, di-n-butyl terephthalate, di-tert-butyl terephthalate, diisobutyl terephthalate, benzyl butyl terephthalate, di-(2-propyl-heptyl) terephthalate monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, di-n-octadecyl terephthalate, diisooctadecyl terephthalate, di-n-eicosyl terephthalate, monocyclohexyl terephthalate, and dicyclohexyl terephthalate.

66. The composition of any of paragraphs 54 through 56, wherein the at least one other plasticizer is selected from the group consisting of at least one of monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate; alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-octadecyl isophthalate, diisooctadecyl isophthalate, di-n-eicosyl isophthalate, monocyclohexyl isophthalate, and dicyclohexyl isophthalate.

67. The composition of any of paragraphs 54 through 56, wherein the at least one other plasticizer is selected from the group consisting of at least one of di-(2-ethylhexyl) adipate and diisononyl adipate.

68. The composition of any of paragraphs 54 through 56, wherein the at least one other plasticizer is selected from the group consisting of at least one of diethylene glycol dibenzoate, butyl benzyl phthalate, dipropylene glycol dibenzoate, phenyl cresyl esters of pentadecyl sulfonic aromatic sulfonic acid esters, tributylacetyl citrate, tri-2-ethylhexyl phosphate, trioctyl phosphate, 2-ethylhexyl-isodecyl phosphate, di-2-ethylhexyl phenyl phosphate, triphenyl phosphate, and tricresyl phosphate.

69. The composition of any of paragraphs 54 through 56, wherein the at least one other plasticizer is a ketal.

70. The composition of paragraph 69, wherein the ketal comprises a formula of:

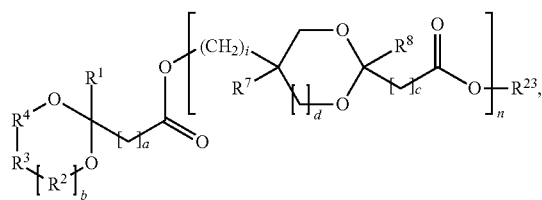
(IV)

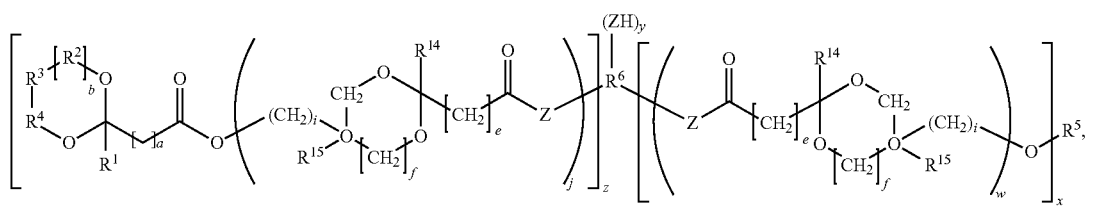
(V)

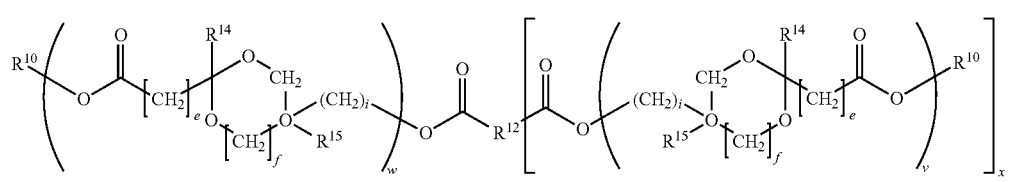
(VI)

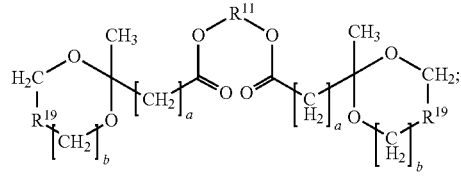
(VII)

or combinations thereof, wherein each a, independently, is from 0 or an integer of 1 to 12;
each b, independently, is 0 or 1;
c is from 0 to 12;
d is 0 or 1;
each e, independently, is from 0 to 12;
each f, independently, is from 0 to 12;
each i is 0 or 1;
each j, independently, is 0 to 100;
each $R^1$, independently, is a hydrogen, a hydrocarbyl group, or a substituted hydrocarbyl group;
each $R^2$, $R^3$ and $R^4$ are independently methylene, alkylmethylene, or dialkylmethylene;
$R^5$ is a hydrogen or

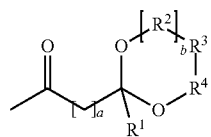

$R^6$ is a hydrocarbyl group or a substituted hydrocarbyl group;
each $R^7$, independently, is a hydrogen, a hydrocarbyl, or a substituted hydrocarbyl group;
each $R^8$, independently, is a hydrogen, a hydrocarbyl, or a substituted hydrocarbyl group;
each $R^{10}$, independently, is a hydrocarbyl or a substituted hydrocarbyl group;

$R^{11}$ is a hydrocarbyl, a substituted hydrocarbyl, or a hydrocarbyl group terminated with one or more heteroatoms to form a cyclic membered ring and which can include one or more of —O—, —NH—, —NR—, wherein R is a hydrocarbyl or a substituted hydrocarbyl;

$R^{12}$, is a covalent bond, a hydrocarbyl group or a substituted hydrocarbyl group;
each $R^{14}$, independently, is a hydrogen, a hydrocarbyl, or a substituted hydrocarbyl group;
each $R^{15}$, independently, is a hydrogen, a hydrocarbyl, or a substituted hydrocarbyl group;
each $R^{19}$, independently, is a hydrocarbyl, a substituted hydrocarbyl, or a hydrocarbyl group substituted with up to 5 hydroxyl groups;
each $R^{23}$ is a hydrocarbyl group or substituted hydrocarbyl group having between 1 and 12 carbon atoms
each Z, independently, is —O—, —NH— or —NR— where R is a hydrocarbyl or a substituted hydrocarbyl group;
n is from 1 to 100;
s is at least one;
v is from 0 to 100;
w is from 1 to 100;
x is at least 1;
y is 0 or a positive number; and
z is 0 or a positive number provided that z is at least one when R5 is hydrogen.

71. The composition of any of paragraphs 54 through 56, wherein the at least one other plasticizer is an ortho phthalate compound.

72. The composition of paragraph 71, wherein the ortho phthalate compound has the structure:

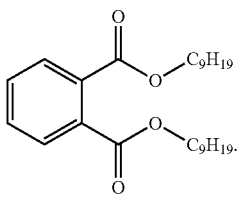

73. The composition of paragraph 71, wherein the ortho phthalate compound has the structure:

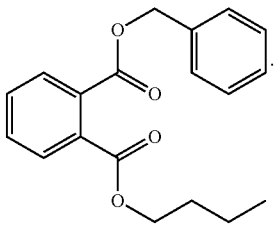 [SMILES: CCCCOC(=O)c1ccccc1C(=O)OCc1ccccc1]

74. The composition of any of paragraphs 54 through 56, wherein the at least one other plasticizer is a terephthalate compound.

75. The composition of paragraph 74, wherein the terephthalate compound has the structure:

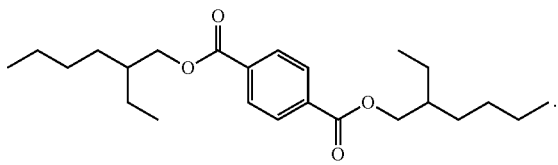 [SMILES: CCCCC(CC)COC(=O)c1ccc(C(=O)OCC(CC)CCCC)cc1]

76. The composition of any of paragraphs 54 through 56, wherein the at least one other plasticizer is a benzoate ester.

77. The composition of paragraph 76, wherein the benzoate ester has the structure:

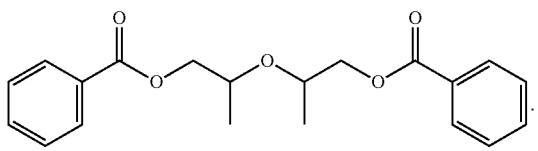 [SMILES: CC(COC(=O)c1ccccc1)OC(C)COC(=O)c1ccccc1]

78. The composition of any of paragraphs 54 through 56, wherein the at least one other plasticizer is a cycloaliphatic compound.

79. The composition of paragraph 78, wherein the cycloaliphatic compound has a structure corresponding to Structure III:

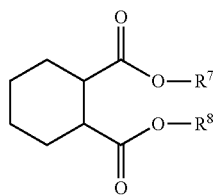

(III)

wherein $R^7$ and $R^8$ are each independently an optionally substituted linear or branched alkyl each having between 6 and 10 carbon atoms.

80. The composition of paragraph 79, wherein the cycloaliphatic compound is selected from the group consisting of:

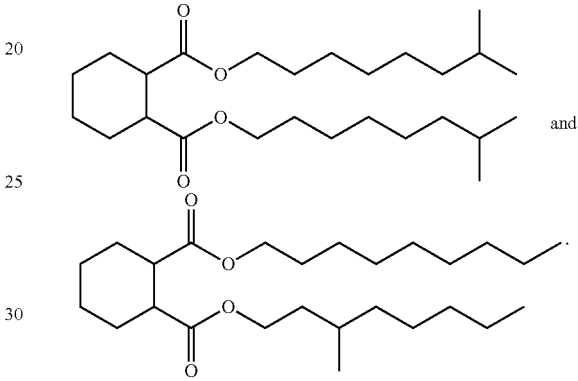

81. The composition of any of paragraphs 54 through 80, wherein the composition comprises from 40 to 180 parts of the compound of any of claims 1 through 34 and the at least one other plasticizer, per 100 parts of the polyvinyl chloride material (parts being by weight).

82. The composition of any of paragraphs 54 through 80, wherein the composition comprises from 70 to 120 parts of the compound of any of claims 1 through 34 and the at least one other plasticizer, per 100 parts of the polyvinyl chloride material (parts being by weight).

83. The composition of any of paragraphs 54 through 80, wherein the blend comprises at least 35% of the compound of any of claims 1 through 34 or the mixture of compounds of any of claims 1 through 34, based upon the total weight of the plasticizer present.

84. The composition of any of paragraphs 54 through 83, wherein the composition further comprises at least one of a stabilizer, a filler, a lubricant, and a processing aid.

85. The composition of any of paragraphs 54 through 84, wherein the polyvinyl chloride material has a K value in the range of from 65 to 75.

86. The composition of claim any of paragraphs 54 through 85, wherein the composition is a dry blend.

87. The composition of claim any of paragraphs 54 through 85, wherein the composition is a plastisol.

The following paragraphs also provide for further still additional aspects of the present invention. In one embodiment, in a eighty eighth paragraph (88), the invention is directed to an article made from the composition of any of paragraphs 54 through 87 (noted as [0183] through [0216]).

89. The article of paragraph 88, wherein the article is selected from the group consisting of coverings, window shades, films, sheetings, upholstery, synthetic leather, shoe soles, shoes, materials used for food contact, adhesive tapes, shoe and automobile interiors, stationary, wires, and cables.

90. The article of paragraph 88, wherein the article is selected from the group consisting of blood bags and medical tubing.

The following paragraphs also provide for further still additional aspects of the present invention. In one embodiment, in a ninety first paragraph (91), the invention is directed to an article produced from the plastisol of paragraph 87, wherein the plastisol is processed through plastisol coating of substrates, dipping, spraying, spreading, rotational molded, casting, or pouring to form the article.

92. The article of paragraph 91, wherein the article is selected from the group consisting of coverings, window shades, films, sheetings, upholstery, synthetic leather, coated cloths and fabrics, toys, shoe soles, shoes, materials used for food contact, adhesive tapes, shoe and automobile interiors, car underbody coatings, wallpaper, stationary, and bottle caps.

The following paragraphs also provide for further still additional aspects of the present invention. In one embodiment, in a ninety third paragraph (93), the invention is directed to an article comprising wire or cable and a coating, said coating comprising PVC and a plasticizer comprising from 30 to 60 wt % based upon the total weight of the plasticizer of a compound of paragraphs 1 through 34.

94. The article of paragraph 93, further comprising a di-isononyl cyclohexanoate ester.

95. The article of either of paragraphs 93 or 94, further characterized as comprising, as plasticizer, at least one compound selected from the group consisting of terephthalate esters, dibenzoate esters, alkyl esters of aromatic tri- or tetra-carboxylic acids, ketal esters and aliphatic dicarboxylic acid esters with monohydric alcohols having 3 to 12 carbon atoms.

The following paragraphs also provide for further still additional aspects of the present invention. In one embodiment, in a ninety sixth paragraph (96), the invention is directed to a car having an interior part comprising PVC and a plasticizer comprising from 30 to 60 wt % based upon the total weight of the plasticizer of a compound of paragraphs 1 through 34.

97. The car of paragraph 96, wherein the plasticizer further comprises a cyclohexane polycarboxylic acid ester.

In one embodiment, in a ninety eighth paragraph (98), the invention is directed to a car having an interior part comprising a composition of any of paragraphs 54 through 87.

In one embodiment, in a ninety ninth paragraph (99), the invention is directed to a film produced from a plastisol comprising PVC and a plasticizer comprising from 30 to 60 wt % based upon the total weight of the plasticizer of a compound of paragraphs 1 through 34.

100. The film of paragraph 99, wherein the plasticizer further comprises a di-isononyl cyclohexanoate ester.

The following paragraphs also provide for further still additional aspects of the present invention. In one embodiment, in a one hundred and first paragraph (101), the invention is directed to a multilayer article in which at least two adjacent layers comprise plasticized polyvinyl chloride wherein the plasticizer in one of said two adjacent layers contains a compound of paragraphs 1 through 34.

102. The multilayer article according to paragraph 101, wherein one of said two adjacent layers contains a phthalate ester.

103. The multilayer article according to paragraph 101, wherein one of said two adjacent layers contains an ester of a cyclohexane polycarboxylic acid.

104. The multilayer article according to paragraph 101, wherein one of said two adjacent layers contains an ester of a terephthalate.

105. The multilayer article according to paragraph 101, wherein one of said two adjacent layers contains an ester of an adipate.

106. The multilayer article according to paragraph 101, wherein one of said two adjacent layers contains an ester of a succinate.

107. The multilayer article according to paragraph 101, wherein one of said two adjacent layers contains an ester of a citrate.

108. The multilayer article according to paragraph 101, wherein one of said two adjacent layers contains an ester of a benzoate.

The following paragraphs also provide for further still additional aspects of the present invention. In one embodiment, in a one hundred and ninth paragraph (109), the invention is directed to an article selected from the group consisting of a medical tubing, a blood bag, a toy and a material used for food contact, said article comprising PVC plasticized with a compound of any of paragraphs 1 through 34, wherein said article comprises a plurality of layers and wherein at least two adjacent layers comprise plasticized polyvinyl chloride wherein the plasticizer in one of said two adjacent layers contains said compound of claims 1 through 30, and wherein the other of said two adjacent layers contains a compounds selected from phthalate esters, dialkyl phthalates, trimethyl pentanyl diisobutyrate, dialkyl isophthalates, dialkyl terephthalates, alkyl benzyl phthalates, alkyl benzyl terephthalates, dibenzyl phthalates, dibenzyl terephthalates, dialkyl adipates, dialkyl succinates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, monobenzoates, dibenzoates, tribenzoates, epoxidized seed oils (such as epoxidized soybean oil or epoxidized linseed oil), chlorinated paraffins, diglycerides, triglycerides, polyketals, and mixtures thereof.

110. The article of paragraph 109, wherein the PVC is plasticized with at least one ester of a cyclohexane dicarboxylic acid, wherein said at least one ester is selected from:

(i) cyclohexane-1,2-dicarboxylic acid di(isononyl) ester, obtainable by hydrogenating the di(isononyl)phthalate having the CAS No. 68515-48-0;

(ii) cyclohexane-1,2-dicarboxylic acid di(isononyl) ester, obtainable by hydrogenating the di(isononyl)phthalate having the CAS No. 28553-12-0, which is based on n-butene;

(iii) cyclohexane-1,2-dicarboxylic acid di(isononyl) ester, obtainable by hydrogenating the di(isononyl)phthalate having the CAS No. 28553-12-0, which is based on isobutene;

(iv) a 1,2-di-C9-ester of cyclohexane dicarboxylic acid, obtainable by hydrogenating the di(nonyl)phthalate having the CAS No. 68515-46-8 or the CAS No. 68515-45-7;

(v) cyclohexane-1,2-dicarboxylic acid di(isodecyl)ester, obtainable by hydrogenating a di(isodecyl)phthalate having the CAS No. 68515-49-1

(vi) a 1,2-di-C9-11-ester of cyclohexane dicarboxylic acid, obtainable by hydrogenating a di-C9-11-phthalate having the CAS No. 98515-43-5;

(vii) a 1,2-di(isodecyl)cyclohexane dicarboxylic acid ester, obtainable by hydrogenating a di(isodecyl)phthalate, consisting essentially of di-(2-propyl-heptyl)phthalate; and (viii) a mixture of diesters of cyclohexanoic dicarboxylic acid with a mixture of alcohols having an average carbon number between 8.5 and 9.5 in whose 1H-NMR spectrum, obtained in deuterated chloroform (CDC13), the ratio of the surface area below the resonance signals with chemical shifts in the range between the lowest valley close to 1.0 and 2.0 towards tetramethylsilane (TMS) to the surface area below the resonance signals with chemical shifts in the range between 0.5 and the lowest valley close to 1.0 ppm towards TMS is between 1.35 and 5.50.

111. The article according to paragraphs 109 or 110, wherein said other of said two adjacent layers contains di-2-ethyl hexyl phthalate as plasticizer.

The following paragraphs also provide for further still additional aspects of the present invention. In one embodiment, in a one hundred and twelfth paragraph (112), the invention is directed to a polyvinyl chloride composition comprising 100 parts of polyvinyl chloride and from 20 to 200 parts of total plasticizer comprising a plasticizer comprising a first compound of paragraphs 1 through 34 and 7 to 30 wt %, based on the weight of the total plasticizer, of a second compound selected from phthalate esters, dialkyl phthalates, trimethyl pentanyl diisobutyrate, dialkyl isophthalates, dialkyl terephthalates, alkyl benzyl phthalates, alkyl benzyl terephthalates, dibenzyl phthalates, dibenzyl terephthalates, dialkyl adipates, dialkyl succinates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, monobenzoates, dibenzoates, tribenzoates, epoxidized seed oils (such as epoxidized soybean oil or epoxidized linseed oil), chlorinated paraffins, diglycerides, triglycerides, polyketals, and mixtures thereof.

113. The composition of paragraph 112, wherein the second compound is diisononyl ester of a cyclohexane dicarboxylic acid.

114. The polyvinyl chloride composition of either of paragraphs 112 or 113, wherein the polyvinyl chloride is characterized by a K value in the range of 65 to 70.

115. The polyvinyl chloride composition of either of paragraphs 112 or 113, wherein the polyvinyl chloride is characterized by a K value above 70.

116. The polyvinyl chloride composition of either of paragraphs 112 or 113, wherein the polyvinyl chloride is characterized by a K value in the range of 60 to 67.

117. A finished article made by a process including at least one step selected from the group consisting of extruding, moulding, and calendering, of a composition according to any of paragraphs 112 through 116.

118. The polyvinyl chloride composition of paragraph 113, wherein the diisononyl ester of a cyclohexane dicarboxylic acid is present in the amount of 10 to 20 wt %, based on the weight of the total plasticizer.

The following paragraphs also provide for further still additional aspects of the present invention. In one embodiment, in a one hundred and nineteenth paragraph (119), the invention is directed to a polyvinyl chloride composition comprising 100 parts of polyvinyl chloride and from 20 to 200 parts of total plasticizer comprising a plasticizer other than an ester of a cyclohexane carboxylic acid and 7 to 30 wt %, based on the weight of the total plasticizer, of a compound of paragraphs 1 through 34.

120. The polyvinyl chloride composition of paragraph 119, wherein said polyvinyl chloride is characterized by a K value in the range of 65 to 70.

121. The polyvinyl chloride composition of paragraph 119, wherein said polyvinyl chloride is characterized by a K value above 70.

122. The polyvinyl chloride composition of paragraph 119, wherein said polyvinyl chloride is characterized by a K value in the range of 60 to 67.

123. A finished article made by a process including at least one step selected from the group consisting of extruding, moulding, and calendering, of a composition according to any of paragraphs 119 through 122.

124. The polyvinyl chloride composition of any of paragraphs 119 through 122, wherein said compound of claims 1 through 34 is present in the amount of 10 to 20 wt %, based on the weight of the total plasticizer.

The following paragraphs also provide for further still additional aspects of the present invention. In one embodiment, in a one hundred and twenty fifth paragraph (125), the invention is directed to a mixture of esters of Structure I,

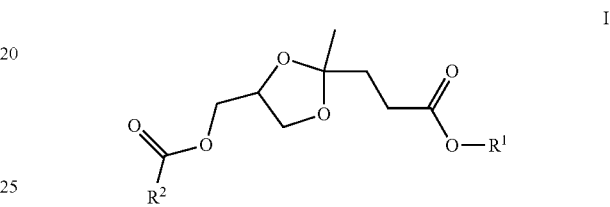

I in which each of $R^1$ and $R^2$ is an aliphatic C5 or C9 moiety, wherein the average chain length of the aliphatic moieties in the mixture is in the range of 5 to 7, and the average degree of branching of the aliphatic C9 moieties is in the range of from 0.9 to 2.2.

126. The mixture of esters according to paragraph 125, further comprising a mixture of trinonyl and tripentyl citrates.

127. The mixture of esters according to paragraph 125, wherein the average chain length of the aliphatic moieties is in the range of from 5.5 to 6.8.

128. The mixture of esters according to paragraph 125, wherein the C5 moieties comprise at least 90% of n-pentyl and 3-methylbutyl moieties, based on the entirety of the C5 moieties.

129. The mixture of esters according to paragraph 125, wherein the C5 moieties comprise at least 70% of 3-methylbutyl moieties, based on the entirety of the C5 moieties.

130. The mixture of esters according to paragraph 125, wherein the average degree of branching of the C9 moieties is from 1.0 to 2.0.

The following paragraphs also provide for further still additional aspects of the present invention. In one embodiment, in a one hundred and thirty first paragraph (131), the invention is directed to a plasticizer composition comprising the mixture of esters according to paragraph 125.

132. The plasticizer composition according to paragraph 131, further comprising at least one plasticizer selected from the group consisting of an alkyl ester of an aromatic polycarboxylic acid, an alkyl ester of a cyclohexanepolycarboxylic acid, an alkyl ester of benzoic acid, an alkyl ester of adipic acid, a dibenzoic ester of a diethylene glycol, a dibenzoic ester of a dipropylene glycol, a dibenzoic ester of a triethylene glycol, a dibenzoic ester of a tripropylene glycol, and a citric ester, wherein the plasticizer composition contains from 15 to 90% by weight of the mixture of esters, the remainder to 100% by weight being the portions by weight of all the plasticizers.

133. A plastics composition, comprising the plasticizer composition according to paragraph 132.

134. A plastics composition according to paragraph 133, comprising polyvinyl chloride (PVC).

135. A plastics composition according to paragraph 133, comprising polyalkyl methacrylate (PAMA).

136. A plastics composition according to paragraph 133, comprising polyvinyl acetate (PVAc).

137. A plastics composition according to paragraph 133, comprising polyvinyl butyral (PVB).

138. A plastics composition according to paragraph 133, comprising polylactic acid (PLA).

139. A plastics composition according to paragraph 133, comprising polyhydroxybutyric acid (PHB).

The following paragraphs also provide for further still additional aspects of the present invention. In one embodiment, in a one hundred and fortieth paragraph (140), the invention is directed to a mixture, comprising: at least two different diesters of Structure I:

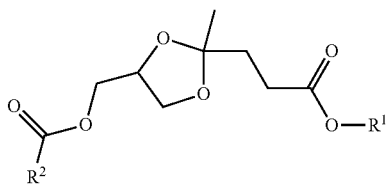

wherein each of $R^1$ and $R^2$ is independently an alkyl group having from 6 to 10 carbon atoms, and $R^1$ and $R^2$ groups of at least two of the diesters of formula I are nonidentical isomers.

141. The mixture of paragraph 140, wherein a proportion of $R^1$ and $R^2$ groups of any one structure is not more than 95 mol % of all $R^1$ and $R^2$ groups in the diesters.

142. The mixture of paragraph 140, wherein less than 10 mol % of $R^1$ and $R^2$ groups in the diesters are 3,5,5-trimethylpentyl groups.

143. The mixture of paragraph 140, wherein the W and $R^2$ groups of the diesters have an average degree of branching of from 0.7 to 2.0.

144. The mixture of paragraph 140, wherein the $R^1$ and $R^2$ groups of the diesters have a degree of branching of from 1.2 to 1.9.

145. The mixture of paragraph 140, wherein the diesters comprise at least two different bicyclic substructures of Structure I, which differ in configuration.

146. The mixture of paragraph 140, wherein the diesters comprise at least two diesters with different molar masses.

147. The mixture of paragraph 140, wherein the diesters comprise at least two diesters of different molar masses, and the diesters comprise at least two different bicyclic substructures of different configurations.

148. The mixture of paragraph 140, wherein the diesters in the mixture all comprise identical bicyclic substructures of Structure I, and individual diester isomers differ only via differently structured $R^1$ and $R^2$ groups.

149. The mixture of paragraph 140, wherein the two different diesters are diesters of isosorbide.

150. The mixture of paragraph 140, further comprising: a polymer, another plasticizer that is not a diester of Structure I, or both.

151. The mixture of paragraph 150, comprising a polymer, wherein a ratio by weight of polymer to diesters of Structure I is from 30:1 to 1:2.5.

152. The mixture of paragraph 150, comprising another plasticizer that is not a diester of Structure I, wherein a molar ratio of the other plasticizer to the diesters of Structure I is from 1:10 to 10:1.

153. The mixture of paragraph 150, comprising a polymer, wherein the polymer is PVC.

In one embodiment, in a one hundred and fifty fourth paragraph (154), the invention is directed to a paint, an ink, a coating, a plastisol, an adhesive, a component of an adhesive, a sealing composition, a plasticizer in a plastic, a plasticizer in a component of a plastic, a solvent, a component of a lubricating oil, or an auxiliary during metalworking, comprising the mixture of paragraph 140.

In one embodiment, in a one hundred and fifty fifth paragraph (155), the invention is directed to a PVC plastic or component thereof, comprising the mixture of paragraph 140.

In one embodiment, in a one hundred and fifty sixth paragraph (156), the invention is directed to a PVC plastisol, comprising the mixture of paragraph 140.

In one embodiment, in a one hundred and fifty seventh paragraph (157), the invention is directed to a PVC composition, comprising: PVC and the mixture of paragraph 140, wherein the composition has a content of from 5 to 250 parts by weight of the mixture of claim 140 per 100 parts by weight of PVC.

In one embodiment, in a one hundred and fifty eighth paragraph (158), the invention is directed to a plastisol, comprising: PVC and the mixture of paragraph 140, wherein the composition has a content of from 5 to 250 parts by weight of the mixture of claim 140 per 100 parts by weight of PVC.

The following paragraphs also provide for further still additional aspects of the present invention. In one embodiment, in a one hundred and fifty ninth paragraph (159), the invention is directed to a method for making an ester compound having Structure I

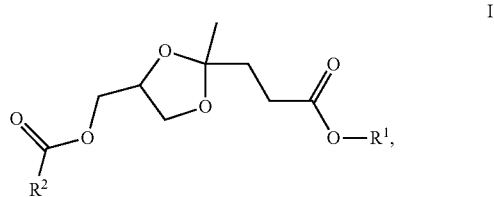

comprising the steps of
contacting reagents comprising one or more alkyl ketal esters having Structure II

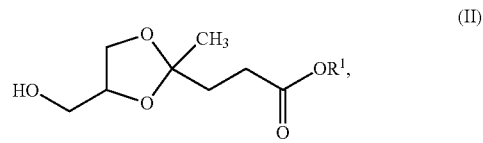

a catalyst and an alkyl halide under reaction conditions to form the compound of Structure I, wherein:
$R^1$ is a linear, branched, or cyclic alkyl or aryl group comprising 2 to 18 carbon atoms and no oxygen atoms, and
$R^2$ is a linear, branched, or cyclic alkyl or aryl group comprising 1 to 17 carbon atoms and no oxygen atoms.

160. The method of paragraph 159, wherein the catalyst is a stoichiometric excess of a catalytic amine or tertiary amine.

161. The method of either of paragraphs 159 or 160 wherein R1 is methyl.

162. The method of either of paragraphs 159 or 160 wherein R1 is ethyl.

163. The method of either of paragraphs 159 or 160 wherein R1 is n-propyl.

164. The method of either of paragraphs 159 or 160 wherein R1 is n-butyl.

165. The method of either of paragraphs 159 or 160 wherein R1 is 2-ethyl-1-hexyl.

166. The method of either of paragraphs 159 or 160 wherein R1 is octyl.

167. The method of either of paragraphs 159 or 160 wherein R1 is dodecyl.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

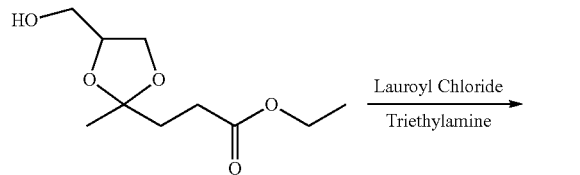

Chemical Formula: $C_{10}H_{18}O_5$
Exact Mass: 218.115
Molecular Weight: 218.247

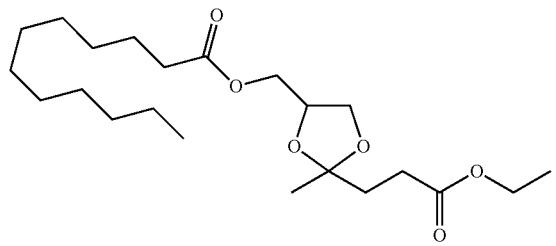

Chemical Formula: $C_{22}H_{40}O_6$
Exact Mass: 400.282
Molecular Weight: 400.549

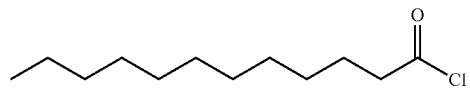

Chemical Formula: $C_{12}H_{23}ClO$
Exact Mass: 218.144
Molecular Weight: 218.763

To a 3 L 3-neck round bottom flask equipped with a mechanical stirrer, temperature probe, addition funnel, and ice-bath was loaded Ethyl LGK (393.8 g, 1.811 mole). Toluene (anhydrous, 1.0 L) and triethyl amine (350 mL, 1.4 eq) were added and the mixture was cooled to <5° C. Lauroyl chloride (414.5 g, 451 mL, 1.05 eq.) was loaded to an addition funnel and was added to the reaction over a 128 minute period while keeping the temperature between 5 and 15° C. A solid formed in the reaction flask. The reaction was stirred 50 minutes after the end of addition and a sample was analyzed at this time to confirm the reaction was complete. The mixture was quenched with methanol (7.5 mL) and left to stir overnight. The mixture was filtered through a medium sintered glass funnel. The solid filtered well. The flask and solid were rinsed with toluene (200 mL×2). The product was rotovapped to give 758.1 g of clear light yellow liquid. The crude product was combined with the crude product from another batch (566 g) which had been prepared according to a similar process. The combined crude product was passed through a wiped film evaporator over a period of 4 hours at 95° C. jacket temperature and between 90 and 180 millitorr vacuum. The product was collected as a bottom product to yield 1221.7 g of liquid. The purity was measured by GC (area %) to be 97.66% and the acid # was 0.95.

Example 2

To a 1 L 3-neck round bottom flask equipped with a mechanical stirrer, temperature probe, addition funnel, and ice-bath was loaded crude Ethyl LGK (87.7 g, 0.403 mole). Toluene (209 mL) and triethyl amine (79 mL, 58 g, 1.4 eq) were added and the mixture was cooled to <5° C. Lauroyl chloride (92.4 g, 1.05 eq.) was loaded to an addition funnel and was added to the reaction over a 90 minute period while keeping the temperature between 5 and 10° C. A solid formed in the reaction flask. The mixture was filtered through a medium sintered glass funnel. The solid filtered well. The flask and solid were rinsed with toluene (100 mL×2). The toluene/product solution was washed with a solution of 0.1 N NaOH combined with 10 wt % NaCl in a separatory funnel to give a slightly cloudy toluene phase and white precipitate in the aqueous phase near the interface. The phases were filtered to remove the precipice, and the toluene phase was passed through a bed of 4 A molecular sieves (41 g, in a column) to give a clear toluene solution. The product was rotovapped to give 161.7 g of liquid with some particulate matter. The solution was filtered through a 1 u glass microfiber filter to give a clear liquid. The liquid (155.4 g) was passed through the wiped film evaporator at 85° C. and 200 mtorr (30 minutes) to give 146.7 g of bottom product. The acid number was measured to be 0.86.

The GC (area %) for each component is shown below in Table 1.

TABLE 1

|  | Toluene | Lights | Product | heavies |
| --- | --- | --- | --- | --- |
| After rotovaporation | 6.66 | 2.04 | 90.3 | 0.97 |
| After WFE | 0 | 1.67 | 97.3 | 1.0 |

Example 3

Amberlyst A35 resin (wet) was decanted from the water slurry and then washed with methanol (×2) and then toluene (×5) until the wash solution did not contain droplets or appear cloudy. To a 1 L round bottom flask was loaded dodecyl LGK (157.3 g), acetic anhydride (70 mL, Alfa Aesar 99+%), toluene (92 g), and washed A35 resin (2.02 g, wet with toluene). The mixture was stirred with an overhead stirrer at 18-20° C. The reaction was allowed to react overnight and samples were taken. The reaction was incomplete at 18 hours and additional acetic anhydride (25 mL) was added. The reaction was stirred an additional 2 hours. Additional acidic resin (1.1 g) was added at about 22 hours of reaction time. After 40 hours of reaction time, the mixture was filtered to remove the resin (392.9 g solution). The mixture was rotovapped at 60° C. and 30-16 torr to remove toluene, acetic acid, and acetic anhydride to yield 197 g of yellow free flowing liquid (Final).

The purity, as measured by GC (area %) for each component is shown below in Table 2.

TABLE 2

| | Component and retention time (minutes) | | | | | | |
|---|---|---|---|---|---|---|---|
| (0) hr | Dodecanol 10.98 | DDLev 14.1 | DDLGK 16.17-16.21 | AcDDLGK 16.5 | Unknown 1 18.1 | Unknown 2 20.5, 20.7 | Unknown 3 20-25 |
| (2 hr) | 0.9 | 13.1 | 43.1 | 35.3 | 0.8 | 0.6 | 4.3 |
| (18 hr) | 1.38 | 12.2 | 8.7 | 73.8 | 0.8 | 0.9 | 2.1 |
| (21 hr) | 1.4 | 12.6 | 3.9 | 75.6 | 0.75 | 0.9 | 3.9 |
| (24 hr) | 1.6 | 13.1 | 3.9 | 77.5 | 0.75 | 0.9 | 1.2 |
| (26 hr) | 1.7 | 13.2 | 2.9 | 78.1 | 0.7 | 0.9 | 0.9 |
| (40 hr) | 2.04 | 13.3 | 0.8 | 79.6 | 0.7 | 0.9 | 1.5 |
| Final | 2.05 | 13.7 | 1.1 | 79.3 | 0.7 | 0.9 | 0.9 |

DDLev = dodecyl levulinate
DDLGK = dodecyl LGK
AcDDLGK = dodecyl LGK acetate (Product) having the structure:

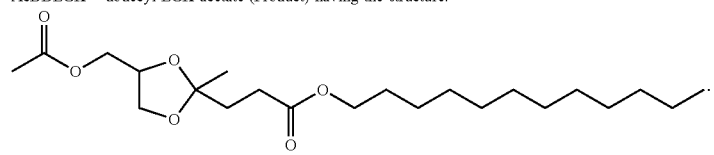

Volatiles were removed by rotovap from the crude AcDDLGK from the (Final) sampling above (195 g), followed by wipe-film evaporation at 140° C. and 0.5-1.6 torr. The material was fed over a period of 50 minutes. Lights (10.1 g, light pass 1) and heavies (143.77 g, heavy pass 1) were collected and analyzed. The heavy pass 1 materials (142.7 g) and 4.7 g of previously made AcDDLGK were combined (147.4 g) and passed through the WFE at 140° C. and 0.3 torr over 40 minutes (3.69 g/min). White waxy solids were observed to build up in the lights exit area and 0.9 g of liquid lights were collected (light pass 2). Heavies (heavy pass 2, 133.43 g) were collected. The heavy product from pass 2 was reloaded to the WFE (132.78 g) and evaporated at 137° C. and 0.3 torr over 30 minutes (4.4 g/min). Lights (light pass 3, 6.6 g) and heavy cut (heavy pass 3, 122.52 g) were collected. Some lights formed solids which were evident near the lights outlet.

The purity, as measured by GC (area %) for each component is shown below in Table 3.

Example 4

To a 1 L 4 neck round bottom flask was added butyl LGK (144.30 g) and toluene (286.6 g). The mixture was tested for water by Karl Fischer titration (377 ppm). The mixture was heated to 111° C. to distill out 3 g of toluene and water. The mixture after water had 0.9 ppm water. Triethylamine (106 mL) was measured with a graduated cylinder and added to the reaction and the mixture was cooled to 2.7° C. in an ice bath. Octanoyl chloride (101.5 g) was added to an addition funnel and gradually added over 75 minutes. The temperature was kept below 20° C. during the addition. The mixture was stirred for 135 minutes after the completion of the addition and a sample was taken. The sample was filtered (0.45μ, PTFE) and diluted with methyl tert-butyl ether. GC analysis showed the reaction was complete. The reaction was left overnight at 15-20° C. The triethylamine hydrochloride salt was removed by filtration and the flask and solid were washed with toluene (50 mL×3) and the filtrate and rinses were combined. The toluene was removed by rotovap to yield 244.7 g of yellow solution which contained 16.4 area % toluene (GC). The product was purified by three passes on a wiped film evaporator. The product was collected as bottoms (Pass 1), bottoms (Pass 2), and overhead (Pass 3) on the three passes. The results are shown in Table 4.

TABLE 3

| | Component and Retention Time (minutes) | | | | | | |
|---|---|---|---|---|---|---|---|
| | Dodecanol | DDLev | DDLGK | AcDDLGK | Unknown 1 | Unknown 2 | Unknown 3 |
| | 10.1-10.98 | 14.1 | 16.17-16.21 | 16.5 | 18.1 | 20.5, 20.7 | 20-25 |
| | 2.05 | 13.7 | 1.1 | 79.3 | 0.7 | 0.9 | 0.9 |
| light pass 1 | 1.1 | 31.0 | 0.48 | 62.9 | 0.25 | 0.02 | 0 |
| heavy pass 1 | 0 | 9.4 | 1.2 | 84.8 | 0.8 | 1.0 | 0.96 |
| (light pass 2) | 30.1 | 20.9 | | 46.4 | 0 | 0 | 0 |
| (heavy pass 2) | 0 | 3.1 | 1.2 | 91.4 | 0.9 | 1.1 | 1.4 |
| (light pass 3) | 0.4 | 17.8 | 0.9 | 79.4 | 0.2 | 0 | 0 |
| (heavy pass 3) | 0 | 1.48 | 1.45 | 92.0 | 1.0 | 1.2 | 1.4 |

TABLE 4

|  | Temp (° C.) | Vac (mtorr) | Bot (g) | OV (g) |
|---|---|---|---|---|
| Pass 1 | 75 | 130 | 210.4 (Product) | 3.35 |
| Pass 2 | 115 | 120 | 195.5 (Product) | 13.4 |
| Pass 3 | 155 | 100 | 32.7 | 160.7 (Product) |

The product collected in pass 3 was analyzed by GC (91.3 area % for two major and 1 minor isomer) and 5.8 area % of a major impurity which is glyceryl trioctanoate.

The Product recovered had the structure

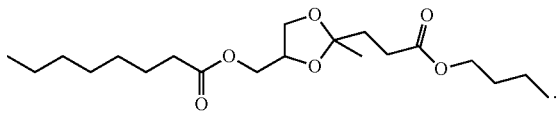 [SMILES: CCCCCCCC(=O)OCC1COC(C)(CCC(=O)OCCCC)O1]

Example 5

To a 3 liter 3-necked flask was added butyl LGK (440.71 g) and pyridine (160 mL) in toluene (1500 mL) and cooled to <5° C. Neat decanoyl chloride (390 mL) was added to the reaction mixture dropwise while the temperature was kept below 30° C. The mixture was allowed to warm for 30 minutes and was quenched with methanol (10 mL). The mixture was filtered on a Buchner funnel to remove pyridine hydrochloride salt, and the solution was concentrated by rotovap to yield the crude product. The crude product was then filtered again to remove additional solids which had precipitated upon concentration. The composition of the crude product (GC area %): 86.4% product, 4.3% toluene, 7.7% butyl levulinate, and 1.6% glyceryl tridecanoate. A second reaction was performed by adding butyl LGK (426.70 g), pyridine (160 mL), and toluene (1500 mL) to a 3 liter 3-necked flask and cooled to <5° C. Neat decanoyl chloride (375 mL) was added to the reaction mixture dropwise while the temperature was kept below 10° C. The mixture was allowed to warm for 30 minutes and was quenched with methanol (10 mL). The mixture was filtered on a Buchner funnel to remove pyridine hydrochloride salt, and the solution was concentrated by rotovap to yield the crude product. The reaction products were combined, and lights were removed by wipe film evaporation (120° C., 70 mtorr) to yield the bottoms product (92.7 GC area %). The wipe film evaporation was repeated on the bottom product (110° C., 60 mtorr) to yield 1158.15 g of product (94.9 GC area %) having the structure:

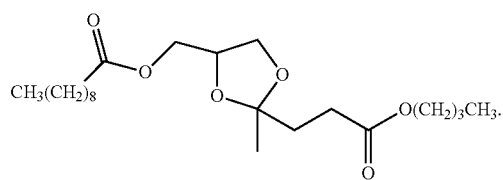

Example 6

To a 2 liter flask was prepared a solution of butyl LGK (172.1 g, 0.70 mol) and triethylamine (138 mL) in toluene (600 mL) and cooled to <10° C. Neat lauroyl chloride (173 mL, 0.75 mol) was added to the reaction mixture dropwise over 95 minutes while the temperature was kept below 10° C. The mixture was warmed to 20° C. and was quenched with methanol (10 mL). The mixture was filtered on a Buchner funnel to remove triethylamine hydrochloride salt, and the solid was washed with 200 mL of toluene. The toluene product solution was washed with water (2×400 mL) to give a solution which was concentrated by rotovap (60° C., 50 torr) to yield 331 of crude product. The composition of the crude product (GC area %): 82.6% product, 13.9% toluene, 2.6% methyl laurate, and 1.0% light others. Lights were removed by wipe film evaporation (120° C., 150 mtorr) to yield 279 g of bottoms product. The wipe film evaporation was repeated on the bottom product at a higher temperature (140° C., 150 mtorr) to yield 268 g of product (97.9 GC area %) having the structure

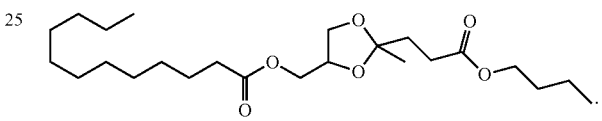

Example 7

To a 1 liter 3-necked flask was added a solution of octyl LGK (168.54 g, 0.56 mol) and triethylamine (105 mL) in toluene (400 mL) and cooled to <5° C. Neat octanoyl chloride (98.04 g) was added to the reaction mixture dropwise over 50 minutes while the temperature was kept below 10° C. The mixture was allowed to warm for 15 minutes and was quenched with methanol (10 mL). The mixture was filtered on a Buchner funnel to remove triethylamine hydrochloride salt, and the solution was concentrated by rotovap to yield the crude product. The crude product was then filtered again to remove additional solids which had precipitated upon concentration. The composition of the crude product (GC area %): 67.37% product, 2.86% toluene, 24.32% octyl levulinate, and other impurities below 1%. Lights were removed by wipe film evaporation (100° C., 150 mtorr) to yield 215.29 g of bottoms product. The wipe film evaporation was repeated on the bottom product at a higher temperature (110° C., 90 mtorr) to yield 193.68 g of product (97.72 GC area %) having the structure

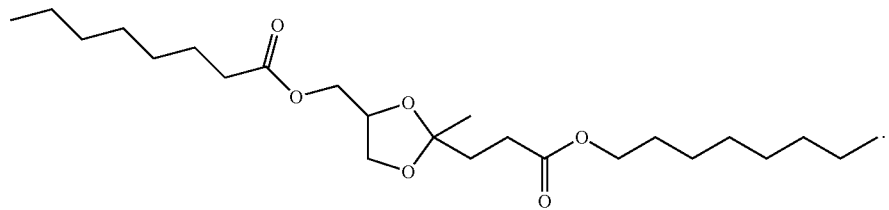 [SMILES: CCCCCCCCOC(=O)CCC1(C)OCC(COC(=O)CCCCCCC)O1]

Example 8

To a 1 L 4-neck round bottom flask equipped with a mechanical stirrer, temperature probe, heating mantle, and condenser with a Dean-Stark trap was loaded 2-ethyl-1-hexyl levulinate (507.7 g, 2.22 mole) and glycerol (69.17 g, 0.75 mol). Amberlyst A35 resin (0.3 g) was added and the mixture stirred at 100° C. and 30 torr. No reaction occurred after 2 hours and two liquid phases were present. Camphorsulfonic acid, 40% solution (0.2 mL) was added and the reaction was heated under vacuum as described in the Table 5 below.

TABLE 5

| Time (minutes) | Pot Temp (C.) | Pressure (C.) | Distillate (mL) | Note |
|---|---|---|---|---|
| 0 | 100 | 30 | 0 | |
| 110 | 100 | 30 | 1 | |
| 115 | 100 | 30 | 1 | |
| 130 | 100 | 30 | 1 | Add 0.2 mL 40% CSA |
| 140 | 100 | 30 | 2/3 | |
| 180 | 100 | 30 | 10/13.5 | |
| 220 | 100 | 30 | 10.5/15 | Sample for GC analysis |
| 315 | 100 | 30 | | Stop Heat |

The reaction sample showed complete reaction by GC with <0.05 area % glycerol. The reaction was cooled and filtered to remove Amberlyst A35 resin. The crude product was 61.3 area % (GC) 2-ethyl-1-hexyl levulinate and 33.8 area % (GC) 2-ethyl-1-hexyl LGK. The reaction product was used as is for the next step.

To a 1 L 4-neck round bottom flask equipped with a mechanical stirrer, temperature probe, addition funnel, and ice-bath was loaded crude 2-ethylhexyl LGK (400.8 g, 40 wt % ethylhexyl LGK, 0.529 mole) in 2-ethyl-1-hexyl levulinate. Triethyl amine (95 mL, 70.4 g, 1.3 eq) was added and the mixture was cooled to <5° C. 2-Ethylhexanoyl chloride (100.2 g, 1.072 eq.) was loaded to an addition funnel and was added to the reaction over a 55 minute period while keeping the temperature between 5 and 10° C. A solid formed in the reaction flask and the mixture was stirred overnight as warmed to room temperature (15° C.). The mixture was filtered through a medium sintered glass funnel. The solid was difficult to filter. The flask and solid were rinsed with toluene (100 mL×3). The toluene/product/2-ethyl-1-hexyl levulinate solution was washed with water in a separatory funnel (100 mL×3) to leave a cloudy mixture. The product was loaded to a 1 L round bottom flask and water and toluene were removed by short path distillation (30 torr, 50° C. up to 70° C.) to give a clear yellow solution. The crude product (422.8 g) was loaded to the wiped film evaporator and processed at 200 to 100 mtorr and 130° C. to yield 175.1 g of bottoms product and 230.4 g of overhead product. The bottoms product contained 2.87 area % (GC) 2-ethyl-1-hexyl levulinate and 94.08 area % (GC) 2-ethyl-1-hexyl LGK-2-ethyl-1-hexanoate product shown below. One group of late eluting peaks constituted 2.06 area % (GC).

The product had the structure:

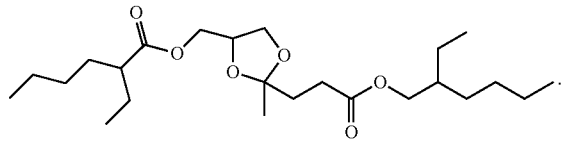 [SMILES: CCCCC(CC)COC(=O)CCC1(C)OCC(COC(=O)C(CC)CCCC)O1]

Example 9

To a 1 liter 3-necked flask was added a solution of 2-ethyl-1-hexyl LGK (150.08 g) and triethylamine (90 mL) in toluene (400 mL) and cooled to <5° C. Neat decanoyl chloride (98.04 g) was added to the reaction mixture dropwise while the temperature was kept below 6° C. GC of the crude product indicated incomplete reaction, and an additional 9 mL of decanoyl chloride was added dropwise. The ice bath was removed and the mixture was allowed to sit overnight (16 h) and was quenched with methanol (5 mL). The mixture was filtered on a Buchner funnel to remove triethylamine hydrochloride salt to give a dark green, opaque solution. 50 g of silica gel was added to the solution, mixed, and filtered off to give an amber colored solution (green color remains on silica gel). The solution was extracted with 100 mL 20% potassium carbonate solution followed by 100 mL saturated sodium chloride solution, and the organic phase dried over magnesium sulfate and filtered. The solution was concentrated by rotovap to yield 238.60 g crude product. Lights were removed by wipe film evaporation (120° C., 60 mtorr) to yield 190.92 g of bottoms product. The wipe film evaporation was repeated on the bottom product at a higher temperature (110° C., 60 mtorr) to yield 182.09 g of dark amber colored product (97 area % GC) having the structure:

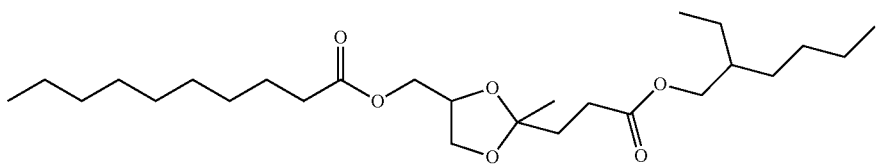

Example 10

To a 2 liter flask was prepared a solution of 2-ethylhexyl LGK (311.8 g, 97% pure, 1.0 mol) and triethylamine (126.5 g, 1.25 mol) in toluene (700 mL) and cooled to <10° C. Neat lauroyl chloride (234.4 g, 1.05 mol) was added to the reaction mixture dropwise over 110 minutes while the temperature was kept below 10° C. The mixture was stirred for 2 hours and was quenched with methanol (25 mL). The mixture was filtered on a Buchner funnel to remove triethylamine hydrochloride salt, and the solid was washed with 200 mL of toluene. The toluene product solution was evaporated by rotovap to remove the majority of the toluene. The concentrated product was filtered through a glass microfiber filter to remove white crystals. The crude product (511.4 g, 13 area % (GC) toluene, 4.4 area % (GC) methyl laurate, 1.6 area % (GC) octyl LGK, 79.4 area % (GC) product) was passed through a wipe film evaporator twice to remove light components. The first pass was conducted at 120° C. and 200 mtorr while the second pass was done at 145° C. and 150 mtorr to yield 500 g of bottoms product. (0.2 area % (GC) methyl laurate, 1.6 area % (GC) 2-ethyl-1-hexyl LGK, 97 area % (GC) product having the structure:

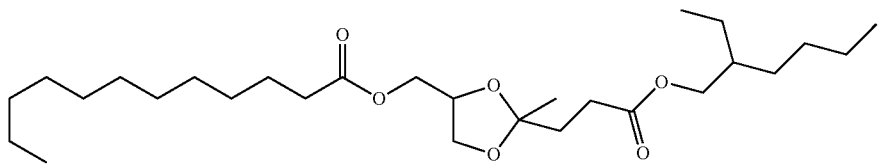

Example 11

To a 3-necked 1 liter round bottom flask was added 162.98 g isononyl-LGK (lot 204-27), 100 ml triethylamine, and 400 ml toluene. An overhead mixer was fitted to one neck of the flask, a thermocouple probe was fitted to a second neck of the flask to measure the temperature of the solution, and an addition funnel was attached to the final neck of the flask. A nitrogen line was fitted to the top of the addition funnel and the flask blanketed with nitrogen, after which the flask was chilled in an ice bath. The addition funnel was charged with 90 ml freshly distilled hexanoyl chloride, which was slowly added to the reaction mixture over the course of 90 minutes such that the reaction temperature was maintained below 10 C. The reaction was allowed to stir for another 15 minutes, then the flask was removed from the ice bath and the reaction quenched by addition of 15 ml methanol and stirring for 30 minutes. Analysis of the crude reaction mixture by GC shows conversion of the isononyl-LGK to be greater than 99%. The solids were removed by filtration, and the solution concentrated by rotary evaporation. Residual volatiles were removed from the product by short path distillation in a wiped-film evaporator to obtain 195.55 g final product, the purity of which was 98.5% by GC-FID. the product had the structure:

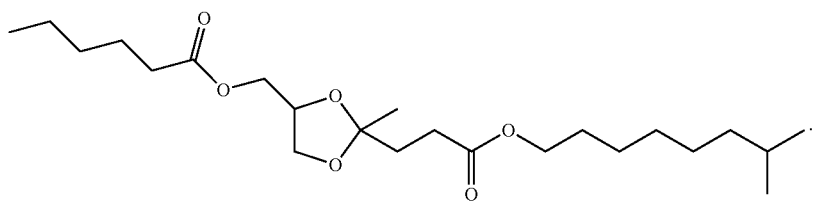 [SMILES: CCCCCC(=O)OCC1COC(C)(CCC(=O)OCCCCCCC(C)C)O1]

Example 12

To a 3-necked 1 liter round bottom flask was added a solution of 148.23 g isononyl-LGK, 85 mL triethylamine, and 400 mL toluene. An overhead mixer was fitted to one neck of the flask, a thermocouple probe was fitted to a second neck of the flask to measure the temperature of the solution, and an addition funnel was attached to the final neck of the flask. A nitrogen line was fitted to the top of the addition funnel and the flask blanketed with nitrogen, after which the flask was chilled in an ice bath. The addition funnel was charged with 100 ml isononanoyl chloride, which was slowly added to the reaction mixture over the course of 90 minutes such that the reaction temperature was maintained below 10 C. GC analysis revealed incomplete reaction, and an additional 18 mL isononanoyl chloride was slowly added. The reaction was allowed to stir for another 15 minutes, then the flask was removed from the ice bath and the reaction quenched by addition of 10 ml methanol and stirring for 15 minutes. The solids were removed by filtration, and the solution concentrated by rotary evaporation. The product was filtered again to remove additional solids that had precipitated upon concentration to yield 242.17 g of a clear yellow colored product. Residual volatiles were removed from the product by short path distillation in a wiped-film evaporator (120° C., 50 mtorr) to obtain 162.25 g final product, the purity of which was 99.0 area % by GC-FID. The product had the structure:

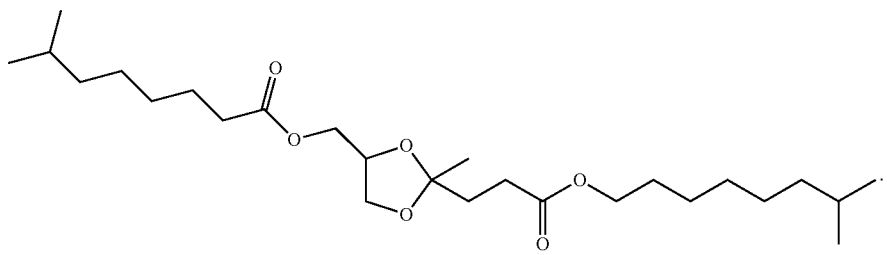 [SMILES: CC(C)CCCCCCOC(=O)CCC1(C)OCC(COC(=O)CCCCCC(C)C)O1]

The present disclosure may suitably comprise, consist of, or consist essentially of, any of the disclosed or recited elements. The disclosure illustratively disclosed herein can be suitably practiced in the absence of any element which is not specifically disclosed herein. The various embodiments described above are provided by way of illustration only and should not be construed to limit the claims attached hereto. It will be recognized that various modifications and changes may be made without following the example embodiments and applications illustrated and described herein, and without departing from the true spirit and scope of the following claims.

We claim:

1. A compound having a structure corresponding to structure I:

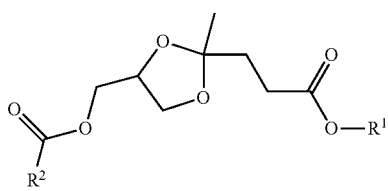

wherein:
R$^1$ is a linear, branched, or cyclic alkyl or aryl group comprising 6 to 12 carbon atoms and no oxygen atoms; and
R$^2$ is a linear, branched, or cyclic alkyl or aryl group comprising 1 to 17 carbon atoms and no oxygen atoms.

2. The compound of claim 1, wherein R$^1$ comprises 8 to 12 carbon atoms.

3. The compound of claim 1, wherein R$^2$ comprises 13-17 carbon atoms.

4. The compound of claim 1, having a structure corresponding to structure Ia:

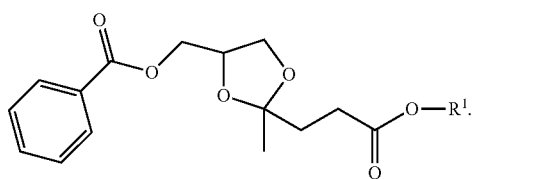

5. The compound of claim 4, wherein Structure (Ia) is selected from the group consisting of:

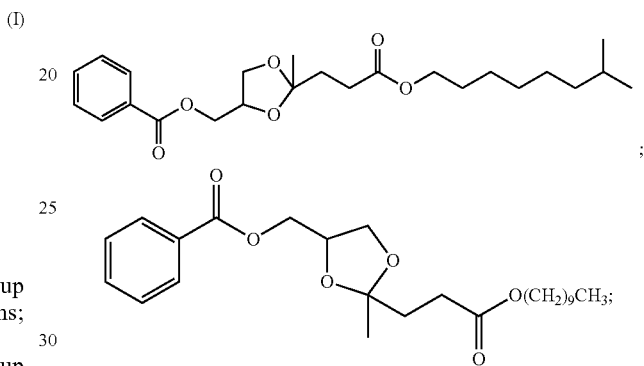

and mixtures thereof.

6. The compound of claim 1, having the structure of:

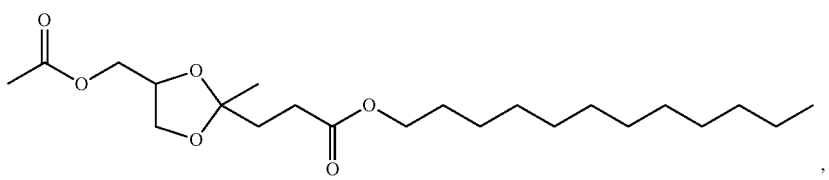

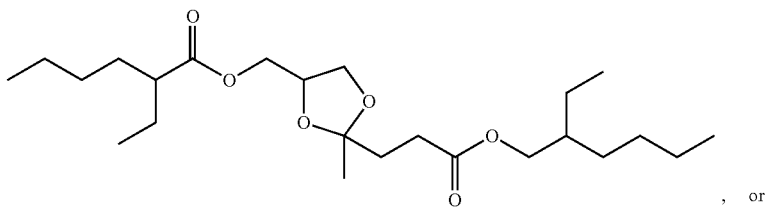

, or

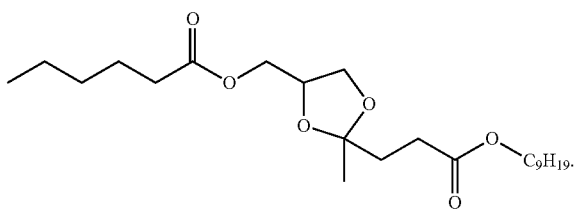

7. The compound of claim 1, wherein Structure I is selected from the group consisting of:
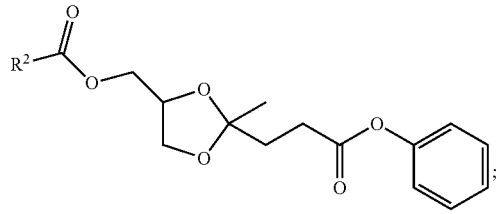
(Ib)
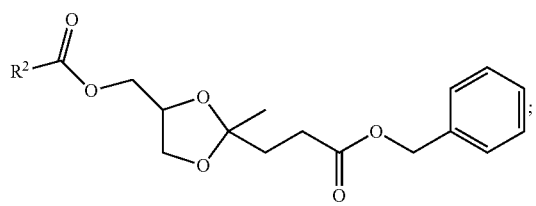
(Ic)
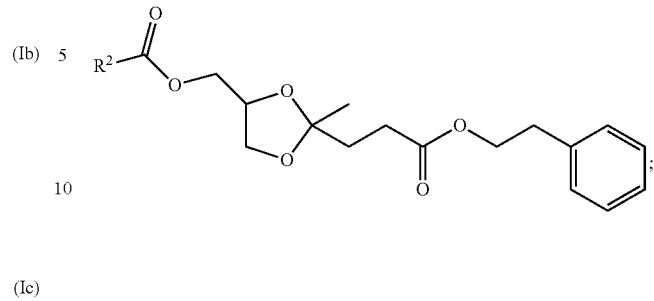
(Id)
and
combinations thereof.
8. The compound of claim 1, having the structure
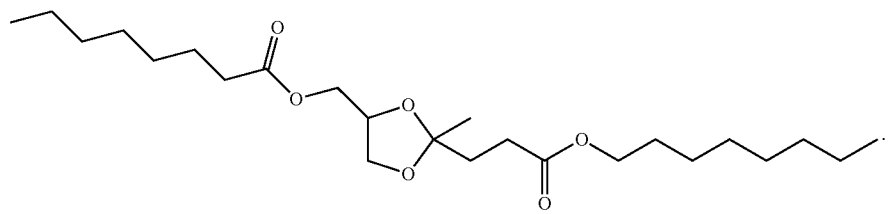 [SMILES: CCCCCCCCOC(=O)CCC1(C)OCC(COC(=O)CCCCCCC)O1]
9. The compound of claim 1, having the structure of
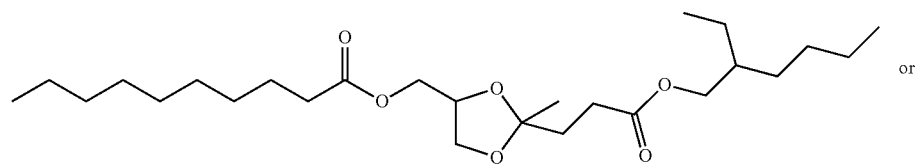
or
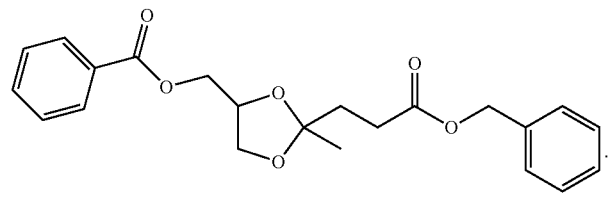
10. The compound of claim 1, having the structure:
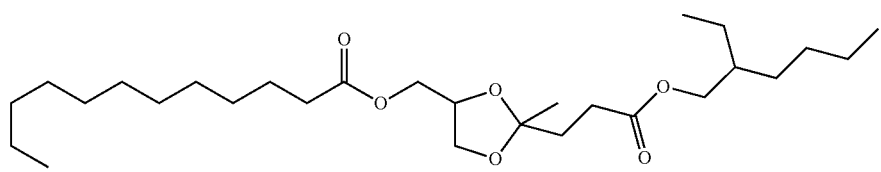

11. The compound of claim 1, having the structure:

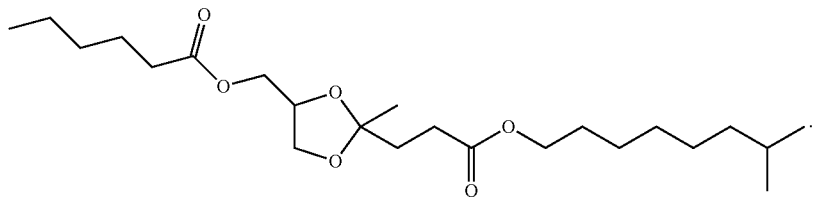 [SMILES: CCCCCC(=O)OCC1COC(C)(CCC(=O)OCCCCCCC(C)C)O1]

12. The compound of claim 1, having the structure:

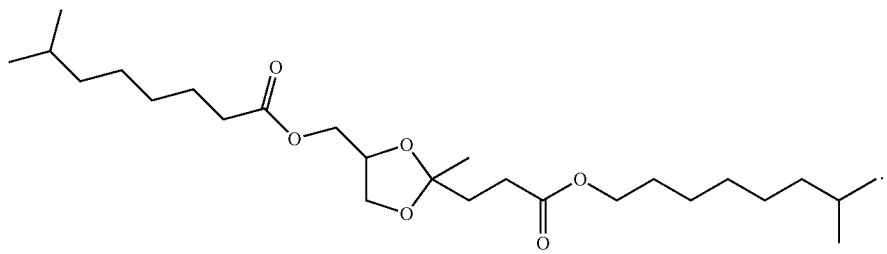 [SMILES: CC(C)CCCCCCOC(=O)CCC1(C)OCC(COC(=O)CCCCCC(C)C)O1]

13. The compound of claim 1, having the structure:

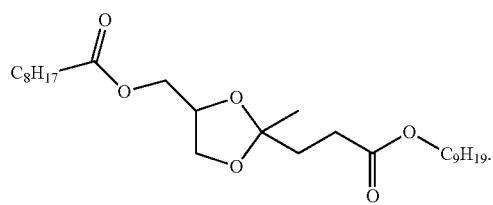

14. A mixture comprising two or more compounds of claim 1.

15. A plasticizer composition comprising a compound of claim 1.

16. A composition comprising:
   (a) a polymer; and
   (b) a compound or mixture of compounds of claim 1.

17. The compound of claim 2, wherein $R^1$ comprises 8 carbon atoms.

18. The compound of claim 1, wherein $R^2$ comprises 11 carbon atoms.

19. The compound of claim 1, wherein $R^1$ is an alkyl group having from 6 to 10 carbon atoms.

* * * * *